United States Patent
Shen et al.

(10) Patent No.: US 6,590,071 B1
(45) Date of Patent: Jul. 8, 2003

(54) REVERSIBLE AQUEOUS PH SENSITIVE LIPIDIZING REAGENTS, COMPOSITIONS AND METHODS OF USE

(75) Inventors: Wei-Chiang Shen, San Marino, CA (US); Hashem Heiati, Sherman Oaks, CA (US)

(73) Assignee: University of Southern California, Los Angeles, CA (US)

( * ) Notice: Subject to any disclaimer, the term of this patent is extended or adjusted under 35 U.S.C. 154(b) by 0 days.

(21) Appl. No.: 09/457,587

(22) Filed: Dec. 9, 1999

Related U.S. Application Data

(60) Provisional application No. 60/111,784, filed on Dec. 10, 1998.

(51) Int. Cl.[7] .................................................. C07K 7/00
(52) U.S. Cl. .................... 530/300; 530/328; 530/214; 530/345; 530/303; 514/2; 514/3; 549/231; 549/262; 435/145; 552/1; 562/553
(58) Field of Search ........................... 549/231, 262; 435/145; 530/214, 345; 562/553

(56) References Cited

U.S. PATENT DOCUMENTS

| | | | |
|---|---|---|---|
| 2,962,504 A | * 11/1960 | Walker | 260/326.5 |
| 4,480,106 A | * 10/1984 | Breitenstein | 549/253 |
| 4,569,789 A | 2/1986 | Blattler et al. | 260/112 |
| 4,618,492 A | 10/1986 | Blattler et al. | 424/85 |
| 4,631,190 A | 12/1986 | Shen et al. | 424/85 |
| 4,751,286 A | 6/1988 | Packard et al. | 530/388 |
| 4,764,368 A | 8/1988 | Blattler et al. | 424/85 |
| 4,786,505 A | 11/1988 | Lovgren et al. | 424/468 |
| 4,853,230 A | 8/1989 | Lovgren et al. | 424/466 |
| 4,889,916 A | 12/1989 | Packard et al. | 525/54.1 |
| 4,935,465 A | 6/1990 | Garman | 525/54.1 |
| 4,997,913 A | 3/1991 | Hellstrom et al. | 530/389 |
| 5,017,693 A | 5/1991 | Hylarides et al. | 530/390 |
| 5,066,490 A | 11/1991 | Neville, Jr. et al. | 424/85.91 |
| 5,140,013 A | * 8/1992 | Gaudreault et al. | 514/21 |
| 5,144,011 A | 9/1992 | Shen et al. | 530/391.5 |
| 5,505,931 A | 4/1996 | Pribish | 424/1.11 |
| 5,563,250 A | 10/1996 | Hylarides et al. | 536/4.1 |
| 5,907,530 A | 5/1999 | Kim et al. | |
| 6,093,692 A | 7/2000 | Shen et al. | 514/3 |

FOREIGN PATENT DOCUMENTS

| | | |
|---|---|---|
| EP | 0 183 503 A | 6/1986 |
| EP | 0 495 265 A | 7/1992 |
| WO | WO 96/22773 | 8/1996 |
| WO | WO 98/13007 | 4/1998 |

OTHER PUBLICATIONS

Wan, J., et al., "Brefeldin A and Monensin Enhance Transferrin Receptor–Mediated Protein Transport Across Epithelial Cells," *Pharmaceutical Research* 8:S–4, Plenum Press (1991).

Apfel, S.C. and Kessler, J.A., "Neurotrophic factors in the therapy of peripheral neuropathy," *Baillière's Clinical Neurology* 4:593–606, Baillière Tindall (1995).

Schröder, E. and Lübke, K., "a. ARG[8]–Vasopressin and LYS[8]–Vasopressin," in: *The Peptides*, Schröder, E. and Lübke, K., eds., Academic Press, New York, pp. 336–350 (1966).

Kayser, M.M. et al., "On the mechanism of Wittig reactions with cyclic anhydrides. II.", *Can. J. Chem.*, 71(7):1010–1021 (1993).

Artursson, P., and Magnusson, C., "Epithelial Transport of Drugs in Cell Culture. II: Effect of Extracellular Calcium Concentration on the Paracellular Transport of Drugs of Different Lipophilicities across Monolayers of Intestinal Epithelial (Caco–2) Cells," *J. Pharm. Sci.* 79:595–600 (1990).

Bikfalvi, A., et al., "Biological Roles of Fibroblast Growth Factor–2," *Endocrine Rev.* 18:26–45 (1997).

Broadwell, R.D., et al., "Transcytotic pathway for blood–borne protein through the blood–brain barrier," *Proc. Natl. Acad. Sci. USA* 85:632–636 (1988).

Brown, E.M., and Aurbach, G.D., "Role of Cyclic Nucleotides in Secretory Mechanisms and Actions of Parathyroid Hormone and Calcitonin," *Vitam. Horm.* 38:205–256 (1980).

Carpenter, G., "EGF: new tricks for an old growth factor," *Curr. Opin. Cell. Biol.* 5:261–264 (1993).

Chu, Y.–C., et al., "High–Potency Hybrid Compounds Related to Insulin and Amphioxus Insulin–like Peptide," *Biochem.* 33: 13087–13092 (1994).

Conradi, R.A., et al., "The Influence of Peptide Structure on Transport Across Caco–2 Cells," *Pharm. Res.* 8:1453–1460 (1991).

Czech, M.P., "Molecular Basis of Insulin Action," *Ann. Rev. Biochem.* 46:359–384 (1977).

Dedon, P.C., and Goldberg, I.H., "Free–Radical Mechanisms Involved in the Formation of Sequence–Dependent Bistranded DNA Lesions by the Antitumor Antibiotics Bleomycin, Neocarzinostatin, and Calicheamicin," *Chem. Res. Toxicol.* 5:311–332 (1992).

(List continued on next page.)

*Primary Examiner*—Christopher S. F. Low
*Assistant Examiner*—David Lukton
(74) *Attorney, Agent, or Firm*—Sterne, Kessler, Goldstein & Fox P.L.L.C.

(57) ABSTRACT

The present invention provides lipidized conjugates comprising an amino group-containing biologically active substance and a lipophilic group capable of penetrating a biological membrane. Under neutral or mildly acidic conditions, including those found in vivo, the free amino group-containing biologically active substance is released from the conjugate by hydrolysis of an amide bond. The present invention is also directed to methods of preparing lipidizing agents and lipidized conjugates, pharmaceutical compositions comprising lipidized conjugates and methods of increasing the delivery of amino group-containing substances into a cell. Preferred amino group-containing substances include peptides, proteins and derivatives thereof.

24 Claims, 11 Drawing Sheets-

OTHER PUBLICATIONS

Edwards, P.A.W., "Is Mucus a Selective Barrier to Macromolecules," *Br. Med. Bull.* 34:55–56 (1978).

Ekrami, H.M., et al., "Water–soluble fatty acid derivatives as acylating agents for reversible lipidization of polypeptides," *FEBS Letters* 371:283–286 (1995).

Fix, J.A., et al., "Acylcarnitines: drug absorption–enhancing agents in the gastrointestinal tract," *Am. J. Physiol.* 251:G332–G340 (1986).

Friden, P.M., and Walus, L.R., "Transport of Proteins Across the Blood–Brain Barrier Via the Transferrin Receptor," in *Frontiers in Cerebral and Vascular Biology: Transport and its Regulation*, Drewes, L.R., and Betz, A.L., eds., Plenum Press, New York pp. 129–136 (1993).

Gonzalez–Mariscal, L., et al., "Tight Junction Formation in Cultured Epithelial Cells (MDCK)," *J. Membrane Biol.* 86:113–125 (1985).

Gordon, G.S., et al., "Nasal absorption of insulin: Enhancement by hydrophobic bile salts," *Proc. Natl. Acad. Sci. USA* 82:7419–7423 (1985).

Haberland, G., and McConn, R., "A rationale for the therapeutic action of aprotinin," *Fed. Proc.* 38:2760–2767 (1979).

Hashimoto, M., et al., "Synthesis of Palmitoyl Derivatives of Insulin and Their Biological Activities," *Pharm. Res.* 6:171–176 (1989).

Holyoake, T.L., "Cytokines at the research–clinical interface: potential applications," *Blood Rev.* 10:189–200 (1996).

Huang, W., et al., "Lipophilic Multiple Antigen Peptide System for Peptide Immunogen and Synthetic Vaccine," *Molec. Immunol.* 31:1191–1199 (1994).

Hughes, A.D., et al., "Platelet–Derived Growth Factor (PDGF): Actions and Mechanisms in Vascular Smooth Muscle," *Gen. Pharmacol.* 27:1079–1089 (1996).

Inagaki, M., et al., "Macromolecular permeability of the tight junction of the human nasal mucosa," *Rhinology* 23:213–221 (1985).

Jonuleit, H., et al., "Cytokines and their effects on maturation, differentiation and migration of dendritic cells," *Arch. Dermatol. Res.* 289:1–8 (1996).

Kabanov, A.V., et al., "Lipid modification of proteins and their membrane transport," *Protein Eng.* 3:39–42 (1989).

Kajii, H., et al., "Fluorescence Study on the Interaction of Salicylate with Rat Small Intestinal Epithelial Cells: Possible Mechanism for the Promoting Effects of Salicylate on Drug Absorption In Vivo," *Life Sci.* 37:523–530 (1985).

Kidron, M., et al., "The Absorption of Insulin from Various Regions of the Rat Intestine," *Life Sci.* 31:2837–2841 (1982).

Kluth, D.C. and Rees, A.J., "Inhibiting Inflammatory Cytokines," *Semin. Nephrol.* 16:576–582 (1996).

Lee, V.H.L., "Enzymatic Barriers to Peptide and Protein Absorption," *Critical Rev. Ther. Drug Delivery Sys.* 5:69–97 (1988).

Lee, V.H.L., et al., "Mucosal Penetration Enhancers for Facilitation of Peptide and Protein Drug Absorption," *Crit. Rev. Ther. Drug Carrier Sys.* 8:91–192 (1991).

Letsinger, R., et al., "Cholesteryl–conjugated oligonucleotides: Synthesis, properties, and activity as inhibitors of replication of human immunodeficiency virus in cell culture," *Proc. Natl. Acad. Sci. USA* 86:6553–6556 (1989).

Majno, P.E., et al., "Mini–Review: Tumor Necrosis Factor (TNF) and TNF Soluble Receptors (TNF–sR) in Liver Disease and Liver Transplantation," *Swiss Surg.* 1:182–185 (1995).

Markwardt, F., "Hirudin as an Inhibitor of Thrombin," in *Methods in Enzymology, vol. XIX, Proteolytic Enzymes*, Perlman, G.E., Lorand, L., eds., Academic Press, New York, pp. 924–932 (1970).

Martins, M.B.F., et al., "Acylation of L–asparaginase with total retention of enzymatic activity," *Biochimie* 72:671–675 (1990).

Moses, H.L., and Serra, R., "Regulation of differentiation by TGF–β," *Curr. Opin. Genet. Dev.* 6:581–586 (1996).

Moss, R.L., "Actions of Hypothalamic–Hypophysiotropic Hormones on the Brain," *Ann. Rev. Physiol.* 41:617–631 (1979).

Mostov, K.E., and Semister, N.E., "Transcytosis," *Cell* 43:389–390 (1985).

Müller, C.E., et al., "Lipophilic disulfide prodrugs—syntheses and disulfide bond cleavage," *Int. J. Pharm.* 57:41–47 (1989).

Muranishi, S., et al., "Lipophilic Peptides: Synthesis of Lauroyl Thyrotropin–Releasing Hormone and its Biological Activity," *Pharm. Res.* 8:649–652 (1991).

Nachtmann, F., et al., "Oxytocin," in *Anal. Prof. Drug Subst.*, vol. 10, Florey, K., ed., Academic Press, New York, NY, pp 563–600 (1981).

Nakao, K., "The natriuretic peptide family," *Curr. Opin. Nephrol. Hypertens.* 2:45–50 (1993).

Paukovits, W.R., et al., "The use of haemoregulatory peptides (pEEDCK monomer and dimer) for reduction of cytostatic drug induced haemopoietic damage," *Cancer Treat. Rev.* 17:347–354 (1990).

Rink, T.J., et al., "Structure and biology of amylin," *Trends. Pharmacol. Sci.* 14:113–118 (1993).

Robert, S., et al., "Fatty Acid Acylation of RNase A Using Reversed Micelles as Microreactors," *Biochem. Biophys. Res. Commun.* 196:447–454 (1993).

Schwabe, C., et al., "Relaxin," in *Recent Progress in Hormone Research*, Greep, R.O., ed., Academic Press, New York, pp. 123–211 (1978).

Sett, R., et al., "Macrophage–Directed Delivery of Doxorubicin Conjugated to Neoglycoprotein Using Leishmaniasis as the Model Disease," *J. Infect. Diseases* 168:994–999 (1993).

Shen, W.–C., and Ryser, H.J.P., "Poly(L–lysine) has different membrane transport and drug–carrier properties when complexed with heparin," *Proc. Natl. Acad. Sci. USA* 78:7589–7593 (1981).

Shen, W.–C., et al., "(C) Means to Enhance Penetration. (3) Enhancement of polypeptide and protein absorption by macromolecular carriers via endocytosis and transcytosis," *Adv. Drug. Deliv. Rev.* 8:93–113 (1992).

Sheppard, M.C., and Stewart, P.M., "Treatment Options for Acromegaly," *Metabolism* 45:63–64 (1996).

Smith, P.L., et al., "(D) Routes of Delivery: Case Studies. (5) Oral absorption of peptides and proteins," *Adv. Drug Delivery Rev.* 8:253–290 (1992).

Spiekermann, K., et al., "Functional features of neutrophils induced by G–CSF and GM–CSF treatment: differential effects and clinical implications," *Leukemia* 11:466–478 (1997).

Spivak, J.L., "The Clinical Physiology of Erythropoietin," *Semin. Hematol.* 30:2–11 (1993).

Stiehm, E.R., "Interferon: Immunobiology and Clinical Significance," *Ann. Rev. Inter. Med. 96*:80–93 (1982).

Strobl, J.S., and Thomas, M.J., "Human Growth Hormone," *Pharmacol. Rev. 46*:1–34 (1994).

Takaroi, K., et al., "The Transport of an Intact Oligopeptide across Adult Mammalian Jejunum," *Biochem. Biophys. Res. Commun. 137*:682–687 (1986).

Taub, M.E., and Shen, W.-C., "Polarity in the Transcytotic Processing of Apical and Basal Membrane–Bound Peroxidase–Polylysine Conjugates in MDCK Cells," *J. Cell. Physiol. 150*:283–290 (1992).

vávra, I., et al., "Antidiuretic Action of 1–Deamino–(8–D–Arginine)–Vasopressin in Unanesthetized Rats," *J. Pharmacol. Exp. Ther. 188*:241–247 (1974).

Větvička, V., and Fornůsek, L., "Limitations of Transmembrane Transport in Drug Delivery," *Critical Rev. Ther. Drug Delivery Sys. 5*:141–170 (1988).

Vitetta, E.S., "Immunotoxins: New Therapeutic Reagents for Autoimmunity, Cancer, and AIDS," *J. Clin. Immunol. 10*:15S–18S (1990).

Wan, J., et al., "Transcellular Processing of Disulfide– and Thioether–Linked Peroxidase–Polylysine Conjugates in Cultured MDCK Epithelial Cells," *J. Cell. Physiol. 145*:9–15 (1990).

Wan, J., et al., "Brefeldin A Enhances Receptor–mediated Transcytosis of Transferrin in Filter–grown Madin–Darby Canine Kidney Cells," *J. Biol. Chem. 267*:13446–13450 (1992).

Yoshikawa, H., et al., "Potentiation of Enteral Absorption of Human Interferon Alpha and Selective Transfer into Lymphatics in Rats," *Pharm. Res. 5*:249–250 (1985).

\* cited by examiner

SEQUENCE LISTING

```
<160> NUMBER OF SEQ ID NOS: 1

<210> SEQ ID NO 1
<211> LENGTH: 9
<212> TYPE: PRT
<213> ORGANISM: Artificial Sequence
<220> FEATURE:
<223> OTHER INFORMATION: Arginine Vasopressin
<220> FEATURE:
<221> NAME/KEY: DISULFID
<222> LOCATION: (4)..(9)
<223> OTHER INFORMATION:

<400> SEQUENCE: 1

Gly Arg Pro Cys Asn Gln Phe Tyr Cys
1               5
```

REVERSIBLE AQUEOUS PH SENSITIVE LIPIDIZING REAGENTS, COMPOSITIONS AND METHODS OF USE

This application claims the benefit of U.S. Provisional Application No. 60/111,784, filed Dec. 10, 1998.

BACKGROUND OF THE INVENTION

1. Field of the Invention

The present invention relates generally to the fields of biology and medicine. More particularly, the present invention is directed to compounds, methods and compositions useful in increasing in mammals the transport and delivery of hydrophilic molecules having an amino group, in particular peptides and proteins.

2. Related Art

Advances in biochemistry have made possible the production of large amounts of therapeutically active and pure proteins and peptides. Currently, the therapeutic effects of most of these agents can be achieved only when they are administered via invasive routes, such as by injection. Since most proteins have very short half lives, effective concentrations of these agents can be maintained only when administered by frequent injections.

Although the administration of protein by injection is the most effective means of their delivery in vivo, patient tolerance of multiple injections is very poor. In addition, drug injection requires training and skill that may not always be transferable to patients. In cases where protein drugs have a life-saving role, the administration by injection can be acceptable by the patients. However, in cases where protein drugs are just one of several possible therapies, injections of proteins and peptides are unlikely to be accepted by the patients. Therefore, alternative routes of protein and peptide delivery need to be developed.

Such alternative routes may include the buccal, nasal, oral, pulmonary, rectal and ocular routes. Without exception, these routes are less effective than the parenteral routes of administration, but are still far more attractive than the parenteral routes because they offer convenience and control to the patients. The oral route is particularly attractive because it is the most convenient and patient-compliant.

Mucosal barriers, which separate the inside of the body from the outside (e.g., gastrointestinal, ocular, pulmonary, rectal and nasal mucosa), comprise a layer of tightly joined cell monolayers which strictly regulate the transport of molecules. Individual cells in barriers are joined by tight junctions which regulate entry into the intercellular space. Hence, the mucosa is at the first level a physical barrier, transport through which depends on either the transcellular or the paracellular pathways (Lee, V. H. L., *Critical Rev. Ther. Drug Delivery Sys.* 5:69–97 (1988)).

Paracellular transport through water filled tight junctions is restricted to small molecules (MW<1 kDa) and is essentially a diffusion process driven by a concentration gradient across the mucosa (Lee, V. H. L., *Critical Rev. Ther. Drug Delivery Sys.* 5:69–97 (1988); Artursson, P. and Magnusson, C., *J. Pharm. Sci.* 79:595–600 (1990)). The tight junctions comprise less than 0.5% of the total surface area of the mucosa (Gonzalez-Mariscal, L. M., et al., *J. Membrane Biol.* 86:113–125 (1985); Vetvicka, V. and Lubor, F., *Critical Rev. Ther. Drug Deliv. Sys.* 5:141–170 (1988)); therefore, they play only a minor role in the transport of protein drugs across the mucosa.

The transcellular transport of small drugs occurs efficiently provided the physicochemical properties of the drug are suited to transport across hydrophobic cell barriers. However, the transcellular transport of proteins and peptides is restricted to the process of transcytosis (Shen, W. C., et al., *Adv. Drug. Deliv. Rev.* 8:93–113 (1992)). Transcytosis is a complex process in which proteins and peptides are taken up into vesicles from one side of a cell, and are subsequently shuttled through the cell to the other side of the cell, where they are discharged from the endocytic vesicles (Mostov, K. E. and Semister, N. E., *Cell* 43:389–390 (1985)). The cell membrane of mucosa barriers is a hydrophobic lipid bilayer which has no affinity for hydrophilic, charged macromolecules like proteins and peptides. In addition, mucosa cells may secrete mucin which can act as a barrier to the transport of many macromolecules (Edwards, P., *British Med. Bull.* 34:55–56 (1978)). Therefore, unless specific transport mechanisms exist for proteins and peptides, their inherent transport across mucosa barriers is almost negligible.

In addition to providing a tight physical barrier to the transport of proteins and peptides, mucosa barriers possesses enzymes which can degrade proteins and peptides before, after, and during their passage across the mucosa. This barrier is referred to as the enzymatic barrier. The enzymatic barrier consists of endo- and exopeptidase enzymes which cleave proteins and peptides at their terminals or within their structure. Enzymatic activity of several mucosa have been studied and the results demonstrated that substantial protease activity exists in the homogenate of buccal, nasal, rectal and vaginal mucosa of albino rabbits and that these activities are comparable to those present in the ilium (Lee, V. H. L., *Critical Rev. Ther. Drug Delivery Sys.* 5:69–97 (1988)). Therefore, regardless of the mucosa being considered, the enzymatic barrier present will feature strongly in the degradation of the protein and peptide molecules.

The N and the C termini of peptides are charged and the presence of charged side chains imparts highly hydrophilic characteristics on these macromolecules. In addition, the presence of charged side chains means that proteins and peptides have strong hydrogen bonding capacities; this H-bonding capacity has been demonstrated to play a major role in inhibiting the transport of even small peptides across cell membranes (Conradi, R. A., et al., *Pharm. Res.* 8:1453–1460 (1991)). Therefore, the size and the hydrophilic nature of proteins and peptides combine to severely restrict their transport across mucosa barriers.

One approach that has been used to alter the physical nature of the mucosa barriers is the use of penetration enhancers. The use of penetration enhancers is based on the disruption of the cell barriers by low molecular weight agents which can fluidize cell membranes (Kaji, H., et al., *Life Sci.* 37:523–530 (1985)), open tight junctions (Inagaki, M., et al., *Rhinology* 23:213–221 (1985)), and create pores in the cell membrane (Gordon, S., et al., *Proc. Natl. Acad. Sci. USA* 82:7419–7423 (1985); Lee, V. H. L., et al., *Crit. Rev. Ther. Drug. Carrier Syst.* 8:91–192 (1991)). The use of these agents leads to a non-specific loss of barrier integrity and can lead to the absorption of a variety of large molecules which can be toxic to cells in vivo.

Protease inhibitors have been co-administered with proteins and peptides and have shown some limited activity in enhancing the absorption of these macromolecules in vivo (Kidron, M., et al., *Life Sci.* 31:2837–2841 (1982); Takaroi, K., et al., *Biochem. Biophys. Res. Comm.* 137:682–687 (1986)). The safety and the long-term effects of this approach have yet to be thoroughly investigated.

The prodrug approach is based on the modification of peptides in a manner that will protect them from enzyme degradation and recognition. This has been achieved by the blockage of vulnerable groups on peptides by amidation and acylation. The prodrug approach has thus far proven useful only for small peptides which have easily identifiable domains of activity.

Reduction in size is another feasible approach to increasing the transport potential of proteins. However, the active sites of proteins need to be mapped before size reduction can be attempted. In general, this approach is difficult to apply to the majority of proteins.

Carrier ligands, by virtue of their properties, can alter the cell uptake and transport characteristics of proteins and peptides. The essence of this approach is that a cell-impermeant protein or peptide is covalently attached to a carrier which is highly transported into cells. The mechanisms through which carrier ligands became endocytosed and transcytosed are important in deciding the suitability of the carrier for enhancing the transport of proteins and peptides. Macromolecular carriers are hydrophilic and do not partition into the membrane. Therefore, the transport of large polymeric carriers into the cells is mediated by the affinity of the carrier for the cell membrane. Generally, the uptake of a macromolecular conjugate starts with binding to the cell membrane. The binding of the carrier to the cells can be specific (e.g., binding of antibodies to cell surface antigens), nonspecific (binding of cationic ligand or lectins to cell surface sugars), or receptor mediated (binding of transferring or insulin to their receptors). Once the carrier is bound to the cell surface, it is taken up into vesicles. These vesicles then become processed stepwise and can be routed to several pathways. One pathway is the recycling of the vesicle back to the membrane. Another pathway, which is destructive to the conjugate, is the fusion with lysosomes. An alternative pathway, and one which leads to the transcytosis of the conjugate, is the fusion of the vesicle with the membrane opposite to the side from which it was derived.

The correct balance between the processes of endocytosis and transcytosis determine the delivery of a protein conjugate to its target. For instance, endocytosis may determine the extent to which a conjugate is taken up by the target cell, but transcytosis determines whether or not a conjugate reaches its target (Shen, W. C., et al., *Adv. Drug. Deliv. Rev.* 8:93–113 (1992)). For successful absorption through the gastrointestinal tract, aconjugate must bind the apical membrane of the gastrointestinal mucosa, become internalized into the mucosa cells, be delivered across the cells, and finally become released from the basolateral membrane.

The current literature contains many reports which demonstrate that nonspecific carriers, such as polylysines (Shen, W. C. and Ryser, H. J. P., *Proc. Natl. Acad. Sci. USA* 78:7589–7593 (1981)) and lectins (Broadwell, R. D., et al., *Proc. Natl. Acad. Sci. USA* 85:632–646 (1988)), and specific carriers, such as transferrin (Wan, J., et al., *J. Biol. Chem.* 257:13446–13450 (1992)), asialoglycoprotein (Seth, R., et al., *J. Infect. Diseases* 168:994–999 (1993)), and antibodies (Vitetta, E. S., *J. Clin. Immunol.* 10:15S–18S (1990)) can enhance the endocytosis of proteins into cells. Reports dealing with transcytotic carriers for proteins are fewer, and very few studies have quantitated the transport of protein conjugates across cell barriers. Wheat germ agglutinin (Broadwell, R. D., et al., *Proc. Natl. Acad. Sci. USA* 85:632–646 (1988)) and an anti-transferrin/methotrexate conjugate (Friden, P. M. and Walus, L. R., *Adv. Exp. Med. Biol.* 331:129–136 (1993)) have been shown to be transcytosed across the blood-brain barrier in vivo. Also, polylysine conjugates of horseradish peroxidase (HRP) and a transferrin conjugate of HRP have been shown to be transcytosed across cell monolayers in vitro (Wan, J. and Shen, W. C., *Pharm. Res.* 8:S-5 (1991); Taub, M. E. and Shen, W. C., *J. Cell. Physiol.* 150:283–290 (1992); Wan, J., et al., *Biol. Chem* 267:13446–13450 (1992)).

Fatty acids, as constituents of phospholipids, make up the bulk of cell membranes. They are available commercially and are relatively cheap. Due to their lipidic nature, fatty acids can easily partition into and interact with the cell membrane in a non-toxic way. Therefore, fatty acids represent potentially the most useful carrier ligand for the delivery of proteins and peptides. Strategies that may use fatty acids in the delivery of proteins and peptides include the covalent modification of proteins and peptides and the use of fatty acid emulsions.

Some studies have reported the successful use of fatty acid emulsions to deliver peptide and proteins in vivo (Yoshikawa, H., et al., *Pharm. Res.* 2:249–251 (1985); Fix, J. A., et al., *Am. J. Physiol.* 251:G332–G340 (1986)). The mechanism through which fatty acid emulsions influence the absorption of proteins and peptides is not yet known. Fatty acid emulsions may open tight junctions, solubilize membranes, disguise the proteins and peptides from the gastrointestinal environment, and carry proteins and peptides across the gastrointestinal mucosa as part of their absorption (Smith, P., et al., *Adv. Drug. Delivery Rev.* 8:253–290 (1992)). The latter mechanism has been proposed, but is inconsistent with current knowledge about the mechanism of fat absorption.

A more logical strategy to deliver proteins and peptides across the gastrointestinal epithelium is to make use of fatty acids as non-specific membrane adsorbing agents. Several studies have shown that a non-specific membrane binding agent linked to a protein can promote the transcytosis of a protein conjugate across cells in vitro (Wan, J., et al.,*J. Cell. Physiol.* 145:9–15 (1990); Taub, M. E. and Shen, W. C., *J. Cell. Physiol.* 150:283–290 (1992)). Fatty acid conjugation has also been demonstrated to improve the uptake of macromolecules into and across cell membranes (Letsinger, R., et al., *Proc. Natl. Acad. Sci. USA* 86:6553–6556 (1989); Kabanov, A., et al., *Protein Eng.* 3:39–42 (1989)). Nonetheless, there have been difficulties in conjugating fatty acids to peptides and proteins, including: (1) the lack of solubility of fatty acids in the aqueous solution for the conjugation reaction; (2) the loss of biological activity of peptides and proteins after fatty acid acylation; and (3) the lack of solubility of fatty acid-conjugated peptides in aqueous solutions (see, e.g., Hashimoto, M., et al., *Pharm. Res.* 6:171–176 (1989); Martins, M. B. F., et al., *Biochimie* 72:671–675 (1990); Muranishi, S., et al., *Pharm. Res.* 6:171–176 (1989); Martins, M. B. F., et al., *Biochimie* 72:671–675 (1990); Muranishi, S., et al., *Pharm. Res.* 8:649–652 (1991); Robert, S., et al., *Biochem. Biophys. Res. Commun.* 196:447–454 (1993)).

Once delivered into the cell, peptides and proteins must be released from their carrier. Published PCT Application Nos. WO 96/22773 and WO 98/13007 disclose the transcellular delivery and release of sulfhydryl-containing peptides and proteins. The cellular absorption of sulfhydryl-containing hydrophilic molecules can be increased by conjugation with a fatty acid through a disulfide linkage. The labile disulfide linkage is easily reduced, providing a mechanism for the release of the hydrophilic compounds from the fatty acid moiety once inside the body.

In addition to disulfide bond reduction, other mechanisms for the release of biologically active hydrophilic compounds from carrier systems include hydrolysis and photolytic bond cleavage. (See for example, U.S. Pat. No. 5,505,931 and references cited therein). Hydrolysis-based delivery systems in which a biologically active amine is conjugated with an organic acid incorporating a monoclonal antibody or other substrate for the targeting of specific cells are known. (See U.S. Pat. Nos. 4,764,368, 4,618,492, 5,505,931 and 5,563,250). After specific binding to the targeted cell, these conjugates deliver the active amine (typically in the form of an amide) inside the cell where hydrolysis (of the amide) releases the free amine inside the cell.

The success of prior art hydrolysis-based delivery systems has inspired the search for improved drug-carrier conjugates capable of delivering a biologically active amino group containing compound to the inside of cells. Improved synthetic strategies and treatment techniques are currently being developed.

SUMMARY OF THE INVENTION

The present invention relates to new drug-carrier conjugates and convenient synthetic strategies for their production. Accordingly, the present invention is directed to synthetic methods, intermediates and ultimately final products useful for the uptake and release of biologically-active amino group containing compounds.

In particular, the invention relates to compounds of general Formula I

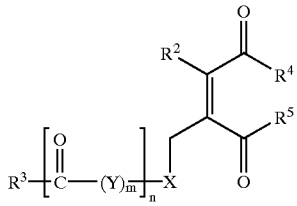

in which $R^2$ is selected from the group consisting of hydrogen, halo, alkyl, or aryl, wherein the alkyl or aryl groups are optionally substituted with one or more alkoxy, alkoxyalkyl, alkanoyl, nitro, cycloalkyl, alkenyl, alkynyl, alkanoyloxy, alkyl or halogen atoms;

$R^3$ is a lipophilic group;

one of $R^4$ and $R^5$ is a biologically active amino group containing substance selected from the group consisting of an amine-containing drug, a natural or unnatural amino acid, a peptide and a protein and the other of $R^4$ and $R^5$ is $OR^6$ where $R^6$ is hydrogen, an alkali metal or a negative charge;

X is oxygen or sulfur;

Y is a bridging natural or unnatural amino acid;

n is zero or 1; and m is an integer from zero to 10.

The present invention also relates to compounds of the general Formula II

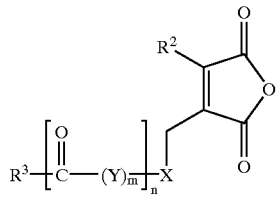

in which $R^2$ is hydrogen, halo, alkyl, or aryl, wherein the alkyl and aryl groups are optionally substituted with one or more alkoxy, alkoxyalkyl, alkanoyl, nitro, cycloalkyl, alkenyl, alkynyl, alkanoyloxy, alkyl or halogen atoms;

$R^3$ is a lipophilic group;

X is O or S;

Y is a bridging natural or unnatural amino acid;

n is zero or 1; and m is an integer from zero to 10.

The present invention also relates to compounds of the general Formula III

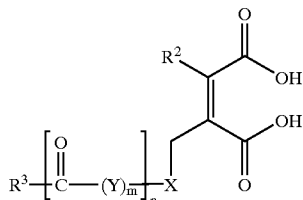

or a pharmaceutically-acceptable salt thereof, in which $R^2$ is hydrogen, halo, alkyl, or aryl, wherein the alkyl and aryl groups are optionally substituted with one or more alkoxy, alkoxyalkyl, alkanoyl, nitro, cycloalkyl, alkenyl, alkynyl, alkanoyloxy, alkyl or halogen atoms;

$R^3$ is a lipophilic group;

X is O or S;

Y is a bridging natural or unnatural amino acid;

n is zero or 1; and m is an integer from zero to 10.

The present invention also relates to methods of forming conjugates of general Formula I from compounds of general Formula II and a biologically active amino group containing substance.

The present invention also relates to methods of forming compounds of general Formula II from maleic acid derivatives and the corresponding thiols or alcohols.

The present invention also relates to methods for increasing the absorption or prolonging blood and tissue retention in a mammal of a biologically active amino group containing substance, in which a conjugate of general Formula I is administered to the mammal in a pharmaceutically-acceptable form.

The present invention also relates to methods for increasing the delivery of hydrophilic amine containing compounds to the inside of a cell having a mucosal barrier, in which a conjugate of general Formula I is contacted with the cell whereby the conjugate penetrates the mucosal barrier of the cell and the free amine is liberated by hydrolysis of an amide bond.

The present invention also relates to pharmaceutical compositions comprising a compound of general Formula I.

The above and other features, advantages, embodiments, aspects and objects of the present invention will be clear to those skilled in the areas of relevant art, based upon the description, teaching and guidance presented herein.

DETAILED DESCRIPTION OF THE INVENTION

Figure 1:
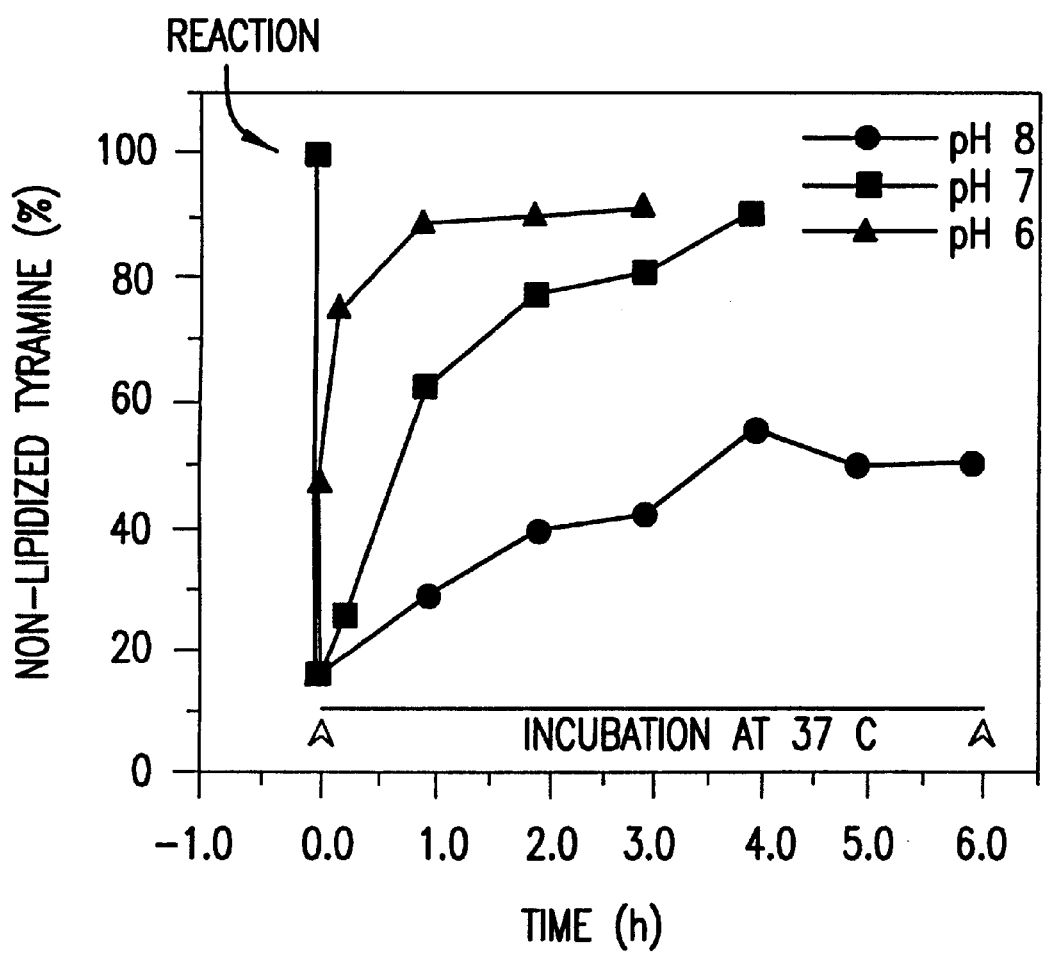
FIG. 1 shows the pH dependence of the release of tyramine from a lipidization carrier reagent (REAL-tyramine) in accordance with the invention. The data show the mean and SD of 3 experiments.

In accordance with the present invention, a biologically active amine containing compound (for example an amino acid, peptide or protein) is attached to a lipophilic derivative via a reversible amide bond. The lipophilic group of such a conjugate binds to the apical side of a cell membrane and facilitates the transport of the conjugate through the cell membrane. Once inside the cell membrane, the biologically active amine containing compound is released into the interstitial fluid as the result of hydrolysis of the amide bond.

Pursuant to one aspect of the present invention, there are provided conjugates of the general Formula I

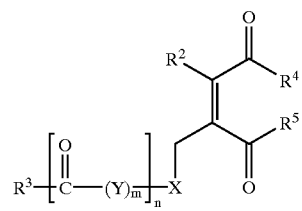

I in which $R^2$ is hydrogen, halo, alkyl, or aryl, wherein the alkyl and aryl groups are optionally substituted with one or more alkoxy, alkoxyalkyl, alkanoyl, nitro, cycloalkyl, alkenyl, alkynyl, alkanoyloxy, alkyl or halogen atoms;

$R^3$ is a lipophilic group;

one of $R^4$ and $R^5$ represent a biologically active amino group containing substance selected from the group consisting of amine-containing drugs, natural or unnatural amino acids, peptides and proteins and the other of $R^4$ and $R^5$ is $OR^6$ where $R^6$ represents hydrogen, an alkali metal or a negative charge;

X is O or S;

Y is a bridging natural or unnatural amino acid;

n is zero or 1; and m is an integer from zero to 10.

Pursuant to another aspect of the present invention, there are provided compounds of the general Formula II

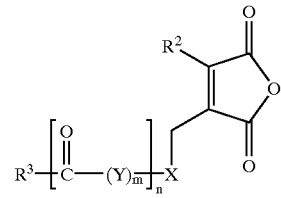

II in which $R^2$ is hydrogen, halo, alkyl, or aryl, wherein the alkyl and aryl groups are optionally substituted with one or more alkoxy, alkoxyalkyl, alkanoyl, nitro, cycloalkyl, alkenyl, alkynyl, alkanoyloxy, alkyl or halogen atoms;

$R^3$ is a lipophilic group;

X is O or S;

Y is a bridging natural or unnatural amino acid;

n is zero or 1; and m is an integer from zero to 10.

Pursuant to another aspect of the present invention, there are provided compounds of the general Formula III

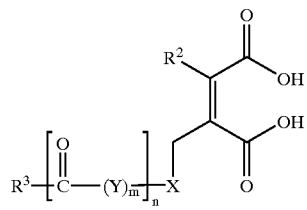

III or a nontoxic pharmaceutically-acceptable salt thereof, in which $R^2$ is hydrogen, halo, alkyl, or aryl, wherein the alkyl and aryl groups are optionally substituted with one or more alkoxy, alkoxyalkyl, alkanoyl, nitro, cycloalkyl, alkenyl, alkynyl, alkanoyloxy, alkyl or halogen atoms;

$R^3$ is a lipophilic group;

X is O or S;

Y is a bridging natural or unnatural amino acid;

n is zero or 1; and m is an integer from zero to 10.

Typical alkyl groups include $C_{1-6}$ alkyl groups including methyl, ethyl, propyl, isopropyl, butyl, isobutyl, sec-butyl, tert-butyl, pentyl, 2-pentyl, 3-pentyl, neopentyl, hexyl, 2-hexyl, 3-hexyl, 2-methyl-1-pentyl, 3-methyl-1-pentyl, 4-methyl-1-pentyl, and the like.

Typical alkoxy groups include oxygen substituted by any of the alkyl groups mentioned above.

Typical alkoxyalkyl groups include any of the above alkyl groups substituted by an alkoxy group, such as methoxymethyl, ethoxymethyl, propoxymethyl, butoxymethyl, pentoxymethyl, hexoxymethyl, methoxyethyl, methoxypropyl, methoxybutyl, methoxypentyl, methoxyhexyl, and the like.

Preferred aryl groups are $C_{6-14}$ aryl groups and typically include phenyl, naphthyl, fluorenyl, phenanthryl, and anthracyl groups.

Typical alkoxy substituted aryl groups include the above aryl groups substituted by one or more of the above alkoxy groups, e.g., 3-methoxyphenyl, 2-ethoxyphenyl, and the like.

Typical alkyl substituted aryl groups include any of the above aryl groups substituted by any of the $C_{1-6}$ alkyl groups, including the group $Ph(CH_2)_n$, where n is 1–6, for example, tolyl, o-, m-, and p-xylyl, ethylphenyl, 1-propylphenyl, 2-propylphenyl, 1-butylphenyl, 2-butylphenyl, t-butylphenyl, 1-pentylphenyl, 2-pentylphenyl, 3-pentylphenyl.

Typical alkenyl groups include $C_{2-6}$ alkenyl groups, e.g. ethenyl, 2-propenyl, isopropenyl, 2-butenyl, 3-butenyl, 4-pentenyl, 3-pentenyl, 2-pentenyl, 5-hexenyl, 4-hexenyl, 3-hexenyl, and 2-hexenyl groups.

Typical alkynyl groups include $C_{2-6}$ alkynyl groups e.g. enthynyl, 2-propenyl, 2-butynyl, 3-butynyl, 4-pentynyl, 3-pentynyl, 2-pentynyl, 5-hexynyl, 4-hexynyl, 3-hexynyl, and 2-hexynyl groups.

Typical alkenyl or alkynyl substituted aryl groups include any of the above $C_{6-14}$ aryl groups substituted by any of the above $C_{2-6}$ alkenyl or $C_{2-6}$ alkynyl groups, e.g., ethenylphenyl, 1-propenylphenyl, 2-propenylphenyl, 1-butenylphenyl, 2-butenylphenyl, 1-pentenylphenyl, 2-pentenylphenyl, 3-pentenylphenyl, 1-hexenylphenyl, 2-hexenylphenyl, 3-hexenylphenyl, ethynylphenyl, 1-propynylphenyl, 2-propynylphenyl, 1-butynylphenyl, 2-butynylphenyl, 1-pentynylphenyl, 2-pentynylphenyl, 3-pentynylphenyl, 1-hexynylphenyl, 2-hexynylphenyl, 3-hexynylphenyl groups.

Typical halo groups include fluorine, chlorine, bromine, and iodine.

Typical halo substituted alkyl groups include $C_{1-6}$ alkyl groups substituted by one or more fluorine, chlorine, bromine, or iodine atoms, e.g., fluoromethyl, difluoromethyl, trifluoromethyl, pentafluoroethyl, 1,1-difluoroethyt, and trichloromethyl groups.

Typical alkanoyl groups include $C_{1-5}C(O)$ alkanoyl groups, e.g., acetyl, propionyl, butanoyl, pentanoyl, and hexanoyl groups, or by an arylalkanoyl group, e.g., a $C_{1-5}C(O)$ alkanoyl group substituted by any of the above aryl groups.

Typical cycloalkyl groups include $C_{3-8}$ cycloalkyl groups including cyclopropyl, cyclobutyl, cyclopentyl, cyclohexyl, cycloheptyl and cyclooctyl groups.

Pursuant to yet another aspect of the present invention, there are provided methods of forming conjugates of general Formula I from compounds of general Formula II and an amino group containing substance.

Pursuant to yet another aspect of the present invention, there are provided methods of forming compounds of general Formula II from maleic acid derivatives and thiols and alcohols.

Pursuant to yet another aspect of the present invention, methods for increasing the absorption or prolonging blood and tissue retention in a mammal of a biologically active amino group containing substance are provided, in which a conjugate of general Formula I is administered to the mammal (for example, in the form of emulsions, nanoparticles (e.g. solid lipid nanoparticles), liposomes, microspheres, microcapsules, aerosols, through inhalation, and transdermal dosage forms).

Pursuant to yet another aspect of the present invention there are provided methods for increasing the delivery of hydrophilic amine containing compounds to the inside of a cell having a mucosal barrier, in which a conjugate of general Formula I is contacted with the cell whereby the conjugate penetrates the mucosal barrier of the cell and the free amine is liberated by hydrolysis of an amide bond.

The term "lipophilic group" as used herein refers to either a naturally occurring lipid per se, a hydrophobic branched or unbranched hydrocarbon comprising about 4 to about 26 carbon atoms, preferably about 5 to about 19 carbon atoms, a fatty acid or ester thereof, or a surfactant. Suitable lipophilic groups include, but are not limited to, long chain alkanoyl groups including: palmityl ($C_{15}H_{31}$), oleyl ($C_{15}H_{29}$), stearyl ($C_{17}H_{35}$), lauryl ($C_{11}H_{23}$), cholyl, and myristyl ($C_{13}H_{27}$).

The term "natural or unnatural amino acid" as used herein refers to any of the 21 naturally occurring amino acids as well as D-form amino acids, blocked L- and D-form amino acids such as those blocked by amidation or acylation, substituted amino acids (e.g., those substituted with a sterically hindered alkyl group or a cycloalkyl group such as cyclopropyl or cyclobutyl) in which the substitution introduces a conformational restraint in the amino acid. The preferred naturally occurring amino acids for use in the present invention as amino acids or components of a peptide or protein are alanine, arginine, asparagine, aspartic acid, citrulline, cysteine, cystine, γ-glutamic acid, glutamine, glycine, histidine, isoleucine, norleucine, leucine, lysine, methionine, ornithine, phenylalanine, proline, hydroxyproline, serine, threonine, tryptophan, tyrosine, valine, γ-carboxyglutamate, or O-phosphoserine. The preferred non-naturally occurring amino acids for use in the present invention as amino acids or components of peptides or proteins are any of the β-amino acids, e.g., β-alanine, α-amino butyric acid, γ-amino butyric acid, γ-(aminophenyl) butyric acid, α-amino isobutyric acid, ε-amino caproic acid, 7-amino heptanoic acid, amino benzoic acid, aminophenyl acetic acid, aminophenyl butyric acid, cysteine (ACM), methionine sulfone, phenylglycine, norvaline, ornithine, δ-ornithine, p-nitro-phenylalanine, 1,2,3,4-terahydroisoquinoline-3-carboxylic acid and thioproline. Also contemplated are amino acid derivatives of the Formula:

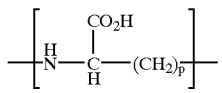

where p is 1–10.

The term "biologically active amino group containing substance" as used herein refers to any substance having biological activity when introduced inside a cell and including in its structure a primary or secondary amine capable of forming an ainide bond through acylation. Substances which do not include a primary or secondary amine may be suitably derivatized so as to be amenable to conjugation with compounds of general Formula II or III. For example, compounds having carboxy groups may be reacted with a suitable diamine, e.g. a $C_2$–$C_{10}$ diamine such as ethylene diamine, propylene diamine, 1,4-diaminobutane, spermine or spermidine and the like in the presence of a compound of general Formula II or III and a water-soluble carbodimide (e.g., EDC) coupling reagent. In this way the diamine serves as means for coupling a biologically active compound, which does not include a primary or second amine, to a compound of general Formula II or m via amide bond formation.

Preferred amine-containing drugs include, but are not limited to, tyramine, arginine vasopressin, insulin (Czech, M. P., *Ann. Rev. Biochem.* 46:359 (1977)), calcitonin (Brown, E. M. and Aurbach, G. D., *Vitam. Horm.* 38:236 (1980)), desmopressin (Vavra, et al., *J. Pharmacol. Exp. Ther.* 188:241 (1974)), interferon-α, -β, and γ (Stiem, E. R., *Ann. Rev. Inter. Med.* 96:80–93 (1982)), interleukin-2, -3, -4, -6, and -11 (Kluth, D. C. and Rees, A. J., Semin. Nephrol. 16:576–582 (1996)); Holyoake, T. L., Blood Rev. 10:169–200 (1996)), G-CSF (Spiekermann, K., et al., *Leukemia* 11:466–478 (1997)), GM-CSF (Jonuleit, H., et al., *Arch. Dermatol. Res.* 289:1–8 (1996)), human growth hormone (Strobl, J. S. and Thomas, M. J., *Pharmacol. Rev.* 46:1–34 (1994)), erythropoietin (Spivak, J. L., *Semin. Hematol.* 30:2–11 (1993)), vasopressin (Schroder, E. and Lubke, K., *The Peptide* 2:336–350 (1966)), octreotide (Sheppard, M. C. and Stewart, P. M., *Metabolism: Clinical and Experimental* 45:63–64 (1996)), aprotinin (Haderland, G. and McConn, R., *Fed. Proc.* 38:2760–2767 (1979)), oxytocin (Nachtmann, F., et al., in *Anal. Prof. Drug Subst.*, Vol. 10, Florey, K., ed., Academic Press, New York, N.Y. (1981), pp. 563–600), β-TGF (Moses, H. L. and Serra, R., *Curr. Opin. Genet. Dev.* 6:581–586 (1996)), BDNF (Apfel, S. C. and Kessler, J. A., *Baillieres. Clin. Neurol.* 4:593–606 (1995)), b-FGF (Bikfalvi, A., et al., *Endocr. Rev.* 18:26–45 (1997)), PDGF (Hughes, A. D., et al., *Gen. Pharmacol.* 27:1079–1089 (1996)), TNF (Majno, P. E., et al., *Swiss. Surg.* 4:182–185 (1995)), atrial natriuretic peptide (Nakao, K., *Curr. Opin. Nephrol. Hypertens.* 2:45–50 (1993)), relaxin (Schwabe, C., et al., *Recent Progr. Horm. Res.* 34:123–211 (1978)), amyrin (Rink, T. J., et al., *Trends. Pharmacol. Sci.* 14:113–118 (1993)), deoxyribonuclease (Laskowski, in *The Enzymes*, Vol. 2, Boyer, P. D., ed., Academic Press, New York, N.Y. (1971), pp. 289–311), EGF (Carpenter, G., Curr. Opin. Cell. Biol. 5:261–264 (1993)), hirudin (Markwardt, *Methods. Enzymol.* 19:924 (1970)), neocarzinostatin (Dedon, P. C. and Goldberg, I. H., *Chem. Res. Toxicol.* 311–332 (1992), hemoregulatory peptide (Paukovits, W. R., et al., *Cancer Treat. Rev.* 17:347–354 (1990)), and somatostatin (Moss, R. L., *Ann. Rev. Physiol.* 41:617 (1979)).

For purposes of the present invention, the term "peptide" refers to natural or unnatural amino acid chains comprising two to 100 amino acids and the term "protein" to natural or unnatural amino acid chains comprising more than 100 amino acids. The proteins and peptides may be isolated from natural sources or prepared by means well known in the art, such as recombinant DNA technology or solid-state synthesis. It is contemplated that the peptides and proteins used in accordance with the present invention may comprise only naturally-occurring L-amino acids, combinations of L-amino acids and other amino acids (including D-amino acids and modified amino acids), or only amino acids other than L-amino acids. In order to form a conjugate of general Formula I, the peptide or protein must bear at least one reactive amine group. The reactive amine group may be part of an amino acid side chain, or a terminal amino group of the peptide or protein backbone, or introduced by chemical modification of functional groups in peptide or protein molecules. Peptides can be homo- or hetero-peptides and can include natural amino acids, synthetic amino acids, or any combination thereof.

Also included within the scope of the present invention are nontoxic pharmaceutically-acceptable salts of the compounds of the invention. In particular, the alkali metal carboxylates, formed by known methods such as the addition of an alkali metal halide to the corresponding carboxylic acid, are contemplated. Such salts include the sodium, potassium, lithium and ammonium salts.

The term "negative charge" as used herein refers to any unsolvated, solvated or complexed lone pair of electrons capable of providing anionic character to a carboxylate group.

The term "alkali metal" as used herein refers to any of the Group I or Group II metals, for example sodium, potassium, lithium, calcium, and magnesium.

The preferred animal subject of the present invention is a mammal. The term "mammal" refers to an individual belonging to the class Mammalia. The invention is particularly useful in the treatment of human patients.

The term "treating" refers to the administration to subjects of a lipidization conjugate for purposes which can include prevention, amelioration, or cure of a disease or condition.

Medicaments are considered to be provided "in combination" with one another if they are provided to the patient concurrently or if the time between the administration of each medicament is such as to permit an overlap of biological activity.

In one preferred embodiment, at least one conjugate is present or administered as part of a pharmaceutical composition.

Pharmaceutical compositions for administration according to the present invention can comprise at least one conjugate according to the present invention in a pharmaceutically acceptable form optionally combined with a pharmaceutically acceptable carrier. These compositions can be administered by any means that achieve their intended purposes. For example, administration may be by oral, parenteral, subcutaneous, intravenous, intramuscular, intraperitoneal, transdermal, intrathecal, intracranial or intranasal routes. The dosage administered will be dependent on the age, health, and weight of the recipient, kind of concurrent treatment, if any, frequency of treatment, and the nature of the effect desired. Amounts and regimens for administration according to the present invention can be determined readily by those with ordinary skill in the art of clinical treatment.

The form of administration may also include emulsions, nanoparticles (e.g., solid lipid nanoparticles), liposomes, microspheres, microcapsules, aerosols, through inhalation, and transdermal dosage forms.

Suitable formulations for parenteral administration include aqueous solutions of the compounds in water-soluble form. In addition, suspensions of the compounds as appropriately oily injection suspensions may be administered. Suitable lipophilic solvents or vehicles include fatty oils, for example, sesame oil, or synthetic fatty acid esters, for example ethyl oleate or triglycerides. Aqueous injection suspensions may contain substances which increase the viscosity of the suspension include, for example, sodium carboxymethyl cellulose, sorbitol, and/or dextran. Optionally, aqueous solutions and/or suspensions may also contain stabilizers and/or buffers, such as borate buffer and the like.

Pharmaceutical preparations of the present invention are manufactured in a manner which is itself known, for example, by means of conventional mixing, granulating, dragee-making, dissolving, or lyophilizing processes. Thus pharmaceutical preparations for oral use can be obtained by combining the active compounds with solid excipients, optionally grinding the resulting mixture, and processing the mixture of granules, after adding suitable auxiliaries, if desired or necessary, to obtain tablets or dragee cores.

Suitable excipients are, e.g., fillers such as saccharide, lactose, sucrose, mannitol or sorbitol; cellulose preparations and/or calcium phosphates, such as tricalcium phosphate or calcium hydrogen phosphate; as well as binders such as starch paste, using, for example, maize starch, wheat starch, rice starch, potato starch, gelatin, tagaranth, methyl cellulose, hydroxypropylmethylcellulose, sodium carboxymethylcellulose, and/or polyvinyl pyrrolidone. If desired, disintegrating agents can be added such as the above-mentioned starches and also carboxymethyl starch, cross-linked polyvinyl pyrrolidone, agar or alginic acid or a salt thereof, such as sodium alginate. Auxiliaries are, above all, flow-regulating agents and lubricants, for example, silica, talc, stearic acid or salts thereof, such as magnesium stearate or calcium stearate, and/or polyethylene glycol. Dragee cores are provided with suitable coatings which, if desired, are resistant to gastric juices. For this purpose concentrated saccharide solutions can be used which can optionally contain gum arabic, talc, polyvinyl pyrrolidone, polyethylene glycol, and/or titanium dioxide, lacquer solutions and suitable organic solvents or solvent mixtures. In order to produce coatings resistant to gastric juices, solutions of suitable cellulose preparations such as acetyl cellulose phthalate or hydroxypropylmethyl cellulose phthalate are used. Coatings may also be provided to protect the lipidization conjugates of the present invention from premature exposure to an acidic environment sufficient to hydrolyze the amide bond formed between the active drug, peptide or protein and the carrier. See U.S. Pat. Nos. 4,786,505 and 4,853,230 for methods of preparing dosage units with cores that are protected from gastric acid. Preferably, the core is neutral or basic.

Basic cores contain one or more alkaline reacting compounds such as those described in U.S. Pat. Nos. 4,786,505 and 4,853,230. Dystuffs or pigments can be added to the tablets or dragee coatings, for example, for identification in order to characterize combinations of active compound doses.

Other pharmaceutical preparations which can be used include, but are not limited to, oral push-fit capsules made of gelatin, rectal suppositories, inhalation formulations for oral and/or nasal administration, nasal or rectal creams or ointments optionally combined with a pharmaceutically acceptable carrier, penetration enhancer, excipient, and/or filler. Penetration enhancers suitable for use include cationic, anionic, amphoteric and neutral penetration enhancers such as benzalkonium chloride, chlorbutanol, AZONE and others known in the art.

Figure 7:
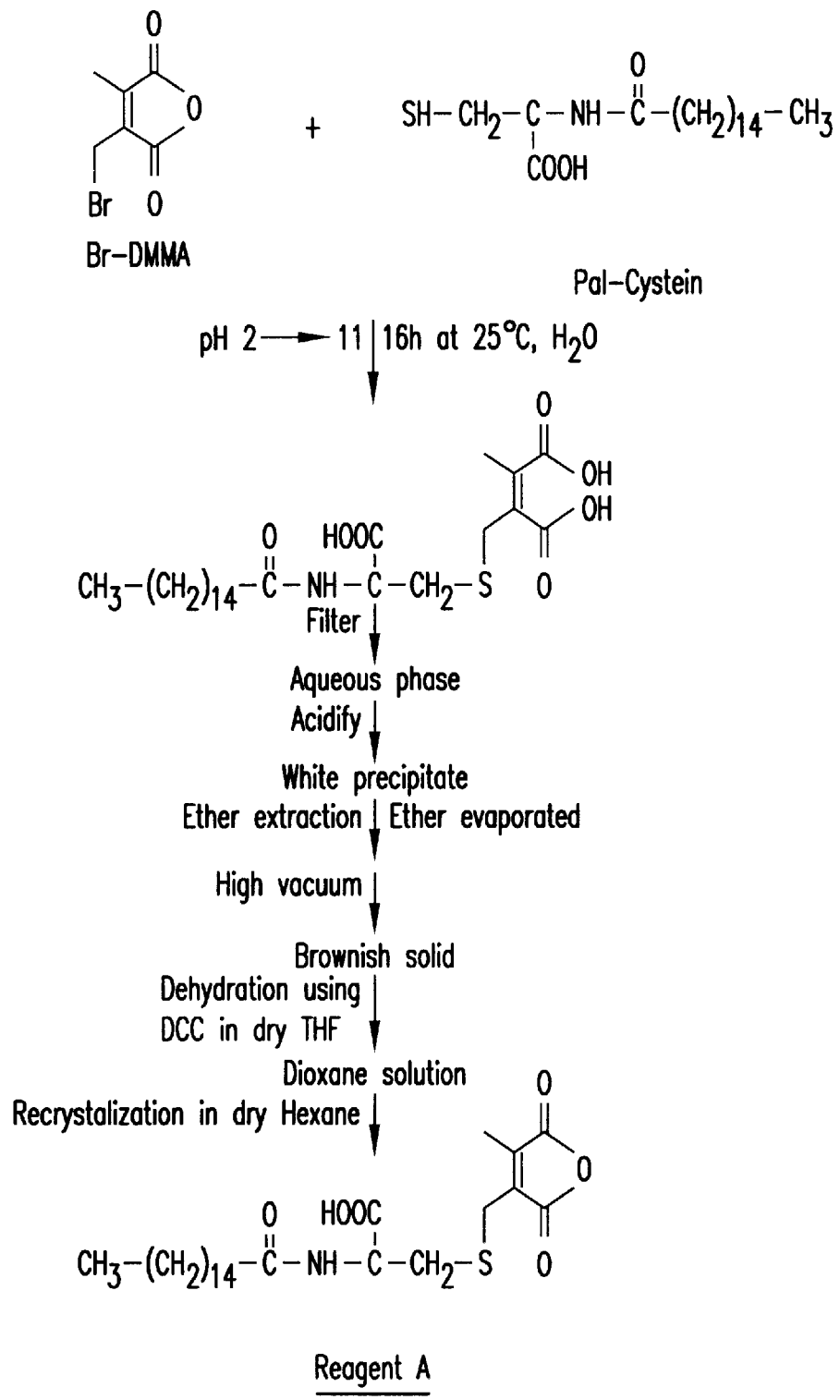
FIG. 7 shows the synthesis of Reagent A (Scheme 1).
Figure 8:
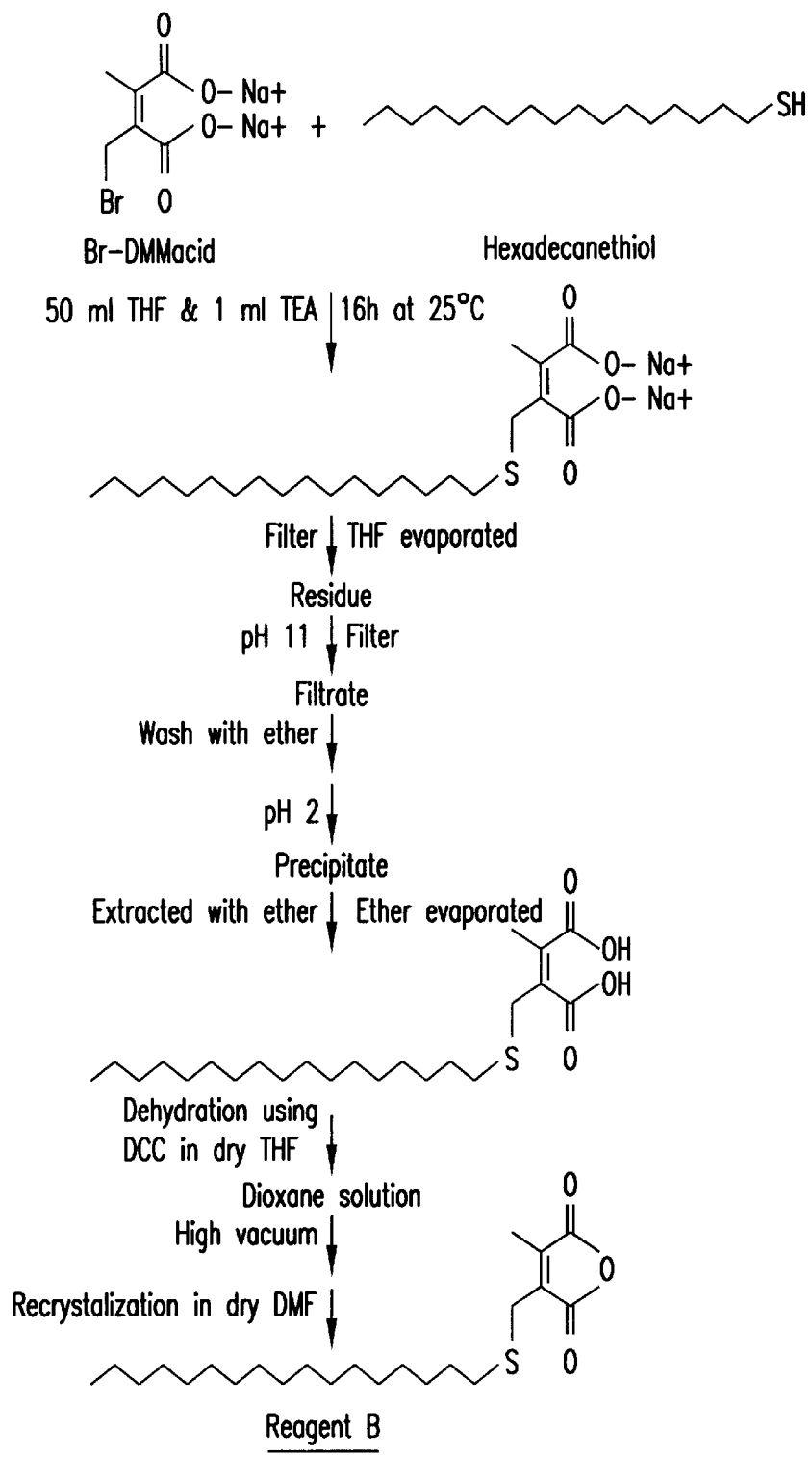
FIG. 8 shows the synthesis of Reagent B (Scheme 2).

The synthesis of exemplary compounds of general Formula II is illustrated in Schemes 1 and 2 (FIGS. 7 and 8). In general, a bromomethyl maleic anhydride derivative, or its maleate salt, is allowed to react with an alcohol or thiol-bearing lipophilic group to form an ether or a thiol ether of general Formula III. The alcohol or thiol-bearing lipophilic group optionally includes a bridging natural or unnatural amino acid moiety bridging the oxygen or sulfur atom and the carbonyl bound to lipophilic group. The bridging natural or unnatural amino acid moiety may be connected to either the oxygen or sulfur atom or the carbonyl bound to lipophilic group at the amino terminus, carboxyl terminus or side chain of the amino acid. With reference to Scheme 1, Pal-cystein effectively includes a glycine bridge bound to the carbonyl at the amino terminus and to the sulfur atom via the side chain. The use of hexadecanethiol as in Scheme 2 represents the formation of compounds of Formula III without the bridging natural or unnatural amino acid. The product of general Formula III is then subjected to dehydrating conditions to reform the maleic anhydride now substituted via the ether or thioether linkage with a lipophilic group, giving compounds of general Formula II. Those skilled in the art will appreciate a variety of alternative synthetic schemes capable of arriving at the desired compounds.

Figure 9:
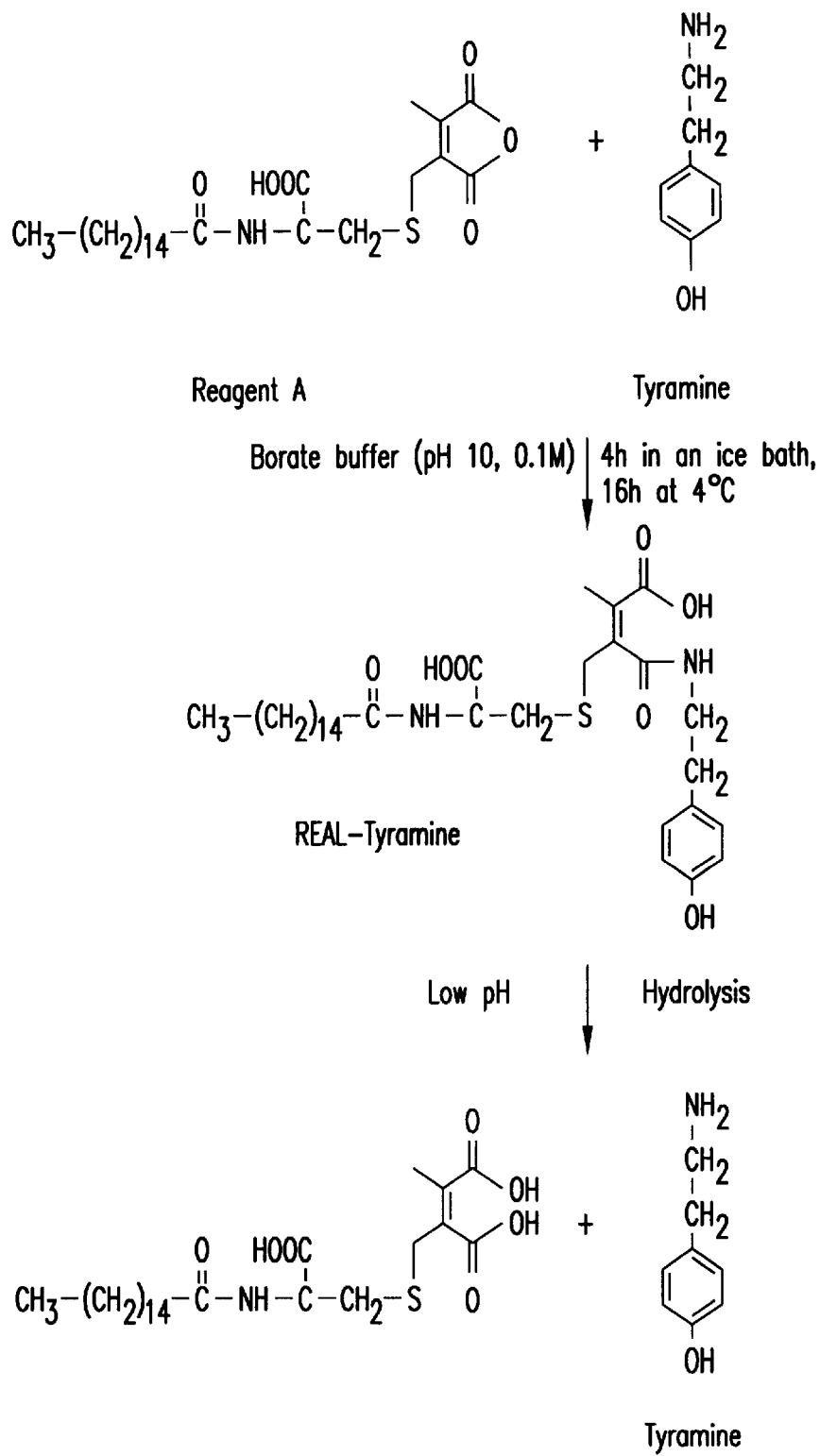
FIG. 9 shows the preparation of reversibly lipidized tyramine (REAL-Tyramine) (Scheme 3).
Figure 10:
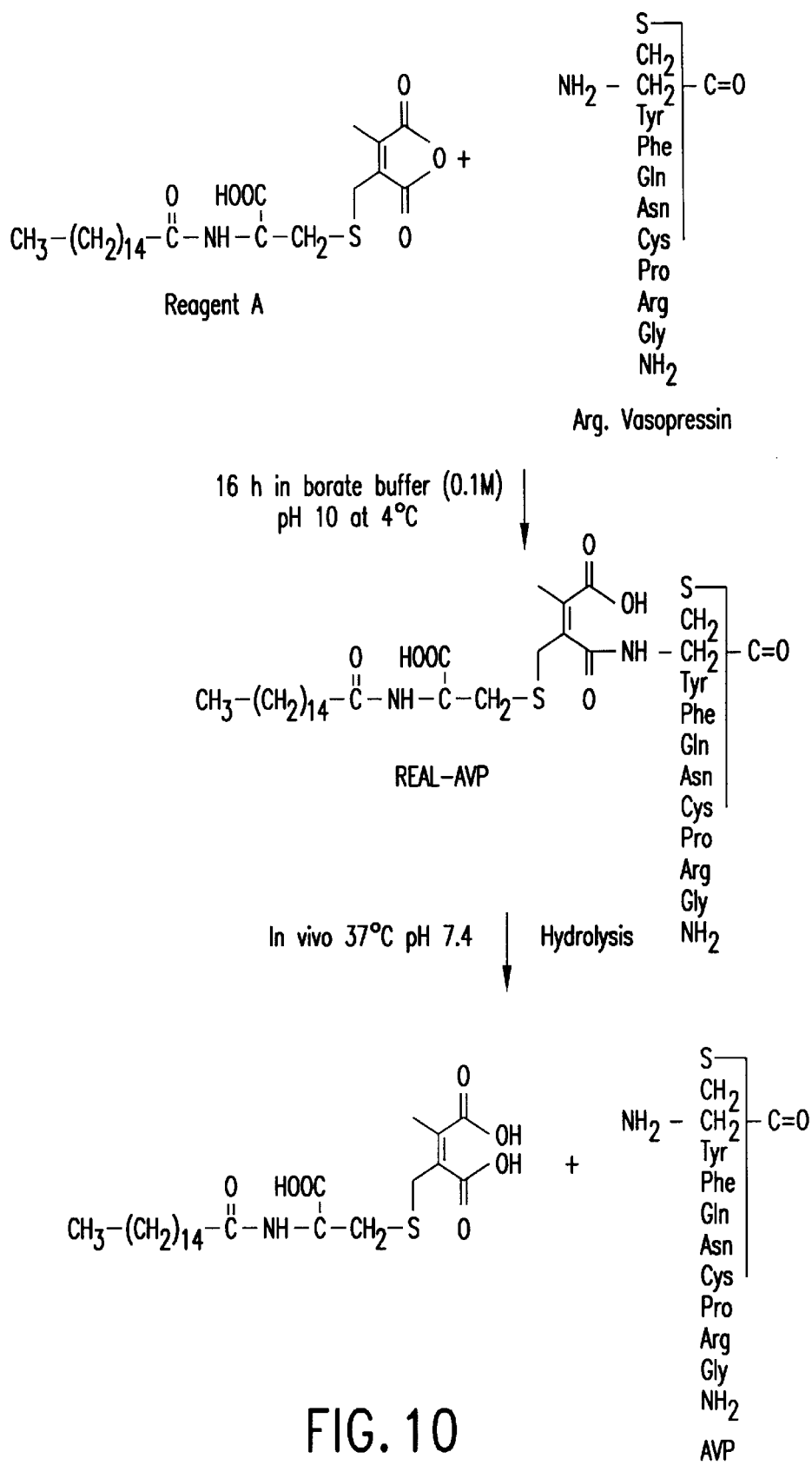
FIG. 10 shows the preparation of reversibly lipidized Arg Vasopressin (REAL-AVP), SEQ ID NO:1 (Scheme 4).
Figure 11:
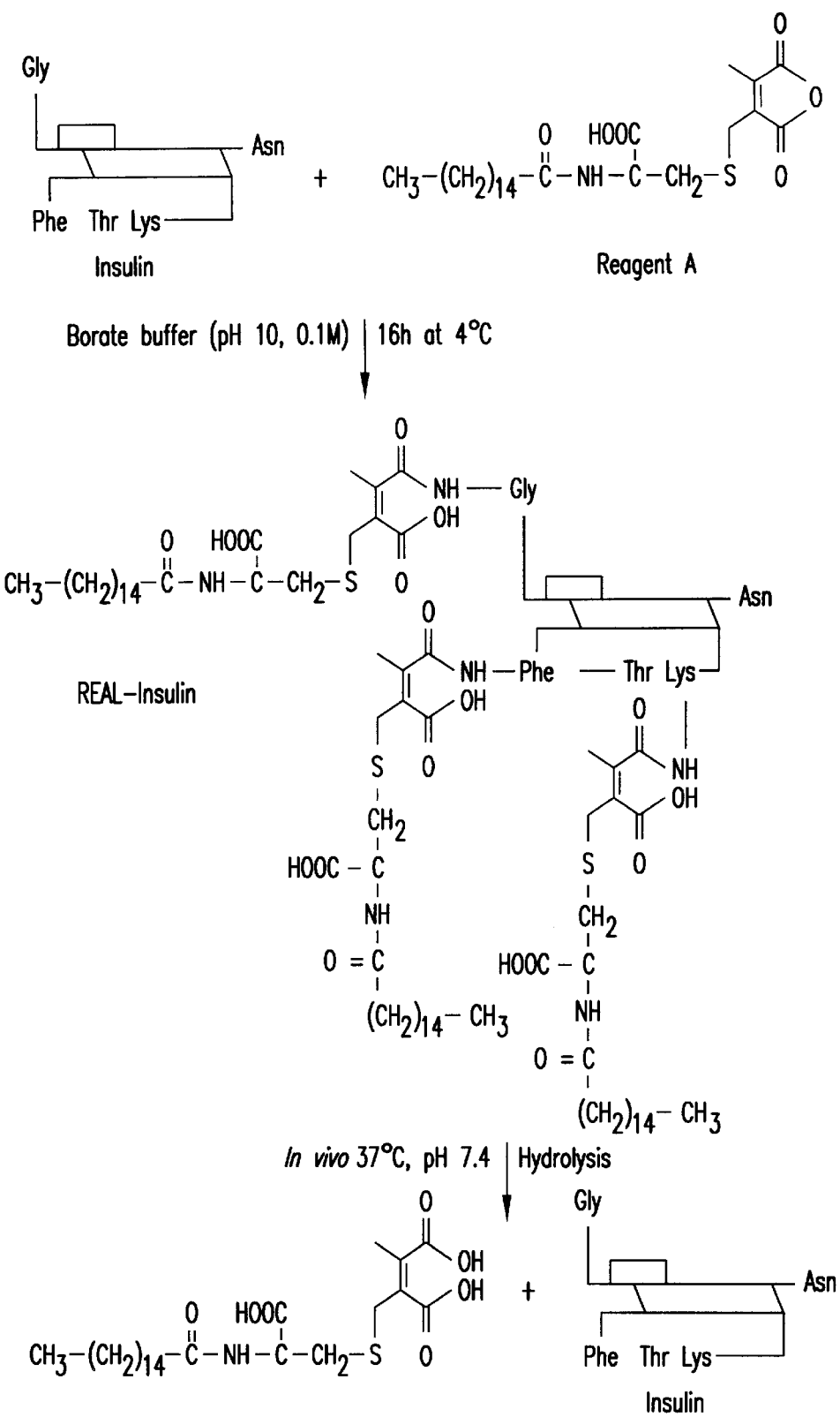
FIG. 11 shows the preparation of reversibly lipidized insulin (REAL-Insulin) (Scheme 5).

Schemes 3–5 (FIGS. 9–11) outline the synthesis of exemplary pH sensitive lipidization conjugates in accordance with the present invention. In general, an amine containing drug, amino acid, peptide or protein is allowed to react with a compound of Formula II to form an amide of Formula I. The amide bond is formed under alkaline conditions, preferably in a buffered aqueous solution. At lower pH, including pH typically found in vivo, the amide bond is hydrolyzed releasing the free amine and a compound of Formula III. Reversible amide bond formation provides a mechanism for the conjugation of a hydrophilic amine with a lipidization reagent at one pH and the release of that amine from the lipidization reagent at a lower pH.

EXAMPLES

Example 1

Synthesis of 3-S-(N-Palmityl Cysteinyl)methyl, 2-Methyl Maleic Anhydride, Reagent A (Scheme 1)

The pyridine disulfide derivative of N-palmityl-cysteine (Pal-CPD) was obtained by known methods. Pal-CPD was synthesized according to the procedure of Ekrami et al., FEBS Letters 371:283–286 (1995). Pal-CPD (0.7 g, 0.00 15 mol) was dissolved in 10 ml NaOH pH 11. Dithiothreitol (DTT) (0.9 g, 0.006 mol) was dissolved in 5 ml water. The Pal-CPD solution was added drop wise to the DTT solution under continuous stirring at room temperature. After 2 h, the reaction was terminated. The pH of the mixture was adjusted to 3 using 0.01N HCl wherein a white precipitate occurred (Pal-cysteine). The precipitate was washed 5 times using diluted HCl to remove the excess amount of DTT.

The starting material 3-bromomethyl, 2-methyl maleic anhydride Br-DMMA) was obtained by the addition of one equivalent of bromide radical to 2,3-dimethyl maleic anhydride (DMMA). Accordingly, DMMA (1.5 g, 0.012 mol), NBS (2.3 g, 0.013 mol), benzoyl peroxide (0.3 g, 0.0012 mol) and magnesium oxide (0.02 g, 0.0005 mol) were heated in 40 ml chloroform under reflux for 4 h. The mixture was filtered and chloroform was evaporated under reduced pressure. To the brown residue 40 ml carbon tetrachloride was added and filtered. The filtrate was collected and the solvent removed under reduced pressure. A clear oil with a light greenish color was obtained which was solidified after storage at 4° C.

With reference to Scheme 1, Br-DMMA is reacted with Pal-cysteine to afford a Pal-cysteine thiol ether of Formula III where $R^1$ is hydrogen, $R^2$ is methyl, $R^3$ is palmityl ($C_{15}H_{31}$), X is sulfur, Y is a glycine radical (—NHCH($CO_2H$)—), n=1 and m=1. The reaction is carried out by adding Br-DMMA (0.3 g, 0.0014 mol) directly to a suspension of Pal-cysteine in 30 ml diluted HCl at room temperature. The pH of the mixture was gradually adjusted to 7, 9 and finally 11, using 1N NaOH. The pH of the mixture was stabilized after 2 h at pH 11. After 16 h stirring at 25° C., the mixture was filtered and the filtrate acidified using 1N HCl. A white precipitate occurred which was extracted with ether. Ether was evaporated under reduced pressure. The remaining greenish oil was dried under high vacuum. 3-S-(N-Palmityl cysteinyl) methyl, 2-methyl maleic acid (420 mg, 0.84 mmol) was obtained with a melting point of 60–63° C. Molar yield was 56%.

3-S-(N-Palmityl cysteinyl) methyl, 2-methyl maleic acid (420 mg, 0.84 mmol) was dissolved in 5 ml dry THF. N,N-Dicyclohexylcarbodiimide (DCC) (692 mg, 3.36 mmol) was dissolved in 1 ml dry THF and added to the above solution in an ice bath. The reaction was stirred in an ice bath for 5 h and then filtered. The filtrate was collected and THF removed under reduced pressure. The residue (brownish solid) was dissolved in 1.5 ml dry dioxane and filtered. The filtrate was added to 30 ml cold dry hexane and kept at 4° C. for 16 h. The precipitate obtained was washed using cold dry hexane and applied to high vacuum in order to remove the solvent. A light brownish product (reagent A) was obtained with a melting point of 46–49° C. Molar yield was 54%.

Example 2

Synthesis of 3S-(hexadecanyl)methyl 2-Methyl Maleic Anhydride, Reagent B (Scheme 2)

With reference to Scheme 2, Br-DMMA is reacted with hexadecanethiol to afford a thiol ether of Formula III where $R^2$ is methyl, $R^3$ is hexadecane ($C_{16}H_{33}$), n=0 and m=0. Under dehydrating conditions, the anhydride reagent B of Formula II is obtained where $R^2$, $R^3$, n and m are as above.

Accordingly, as outlined in Scheme 2, Br-DMMA (0.5 g, 0.0025 mol) was hydrolyzed in 10 ml water at pH 8 and added to 0.63 g hexadecanethiol (0.0025 mol) dissolved in 50 ml THF. Triethylamine (1 ml) was added to the mixture and stirred for 16 h at room temperature. The reaction mixture was filtered and the filtrate was evaporated under reduced pressure. The residue obtained was dissolved in diluted NaOH solution (pH 11) and washed with ether (3×20 mL). The filtrate was adjusted to pH 2 using 1 N HCl and a white precipitate occurred. The precipitate was extracted into ether and the ether removed under reduced pressure. The final product, 3-(hexadecanylthio)methyl 2-methyl maleic acid, was dried under high vacuum.

3-(Hexadecanylthio)methyl 2-methyl maleic acid was dehydrated to give reagent B using the same procedure as previously described for reagent A. Reagent B was dissolved in hot DMF and kept at 4° C. for 16 h. A white precipitate was occurred which was washed using cold DMF. The solvent was removed under high vacuum. A white powder (73 mg) was obtained with a molar yield of 16%.

Example 3

Preparation of Reversibly Lipidized Tyramine (REAL-Tyramine) Using Reagent A (Scheme 3)

Reagent A (2 mg, 0.00426 mmol) was dissolved in 60 µl dry DMF and added to 0.2 mg (0.00146 mmol) tyramine in 200 µl borate buffer USP (pH 10, 0.1M) in an ice bath. The reaction was carried out for 4 h in an ice bath and 16 h at 4° C.

Example 4

Determination of pH Sensitivity of REAL-Tyramine

The pH dependence of amide bond formation was determined by monitoring the concentration of free tyramine. Phosphate buffers 1M at pH 6, 7 & 8 were prepared. REAL-tyramine was diluted 1:2 using these buffers. The stock solution of tyramine was also diluted to have the same concentration of REAL-tyramine and used as control. Samples were incubated at 37° C. Fluorescence of the free tyramine released from REAL-tyramine was determined at different time points using fluorescamine reaction.

After lipidization of tyramine, the concentration of free tyramine decreases up to 15% of the original concentration. Incubation of the REAL-tyramine at low pH resulted in an increase in the concentration of free tyramine indicating the cleavage of the amide bond. The rate of hydrolysis of the amide bond was dependent on the pH, (pH 6>pH 7>pH 8). After 1 h incubation of REAL-tyramine at pH 6 amide bond was almost fully hydrolyzed however, at pH 7 about 45% and at pH 8 only 7% of the amide bond of REAL-tyramine was hydrolyzed (FIG. 1).

Example 5

Preparation of Reversibly Lipidized AVP (REAL-AVP) Using Reagent A (Scheme 4)

Arginine vasopressin (AVP) (0.5 mg) was dissolved in 1 ml borate buffer (pH 10, 0.1M). An aliquot of 0.5 ml (0.25 mg, 0.207 µmol) of this solution was reacted in an ice bath with 1 mg (2.1 µmol) reagent A dissolved in 50 µl dry dimethylformamide (DMF). The mixture was stirred for 16 h at 4° C. The final concentration of REAL-AVP was 0.455 mg/ml.

Example 6

In Vivo Effect of REAL-AVP in Vasopressin Deficient Brattleboro Rats

Figure 2:
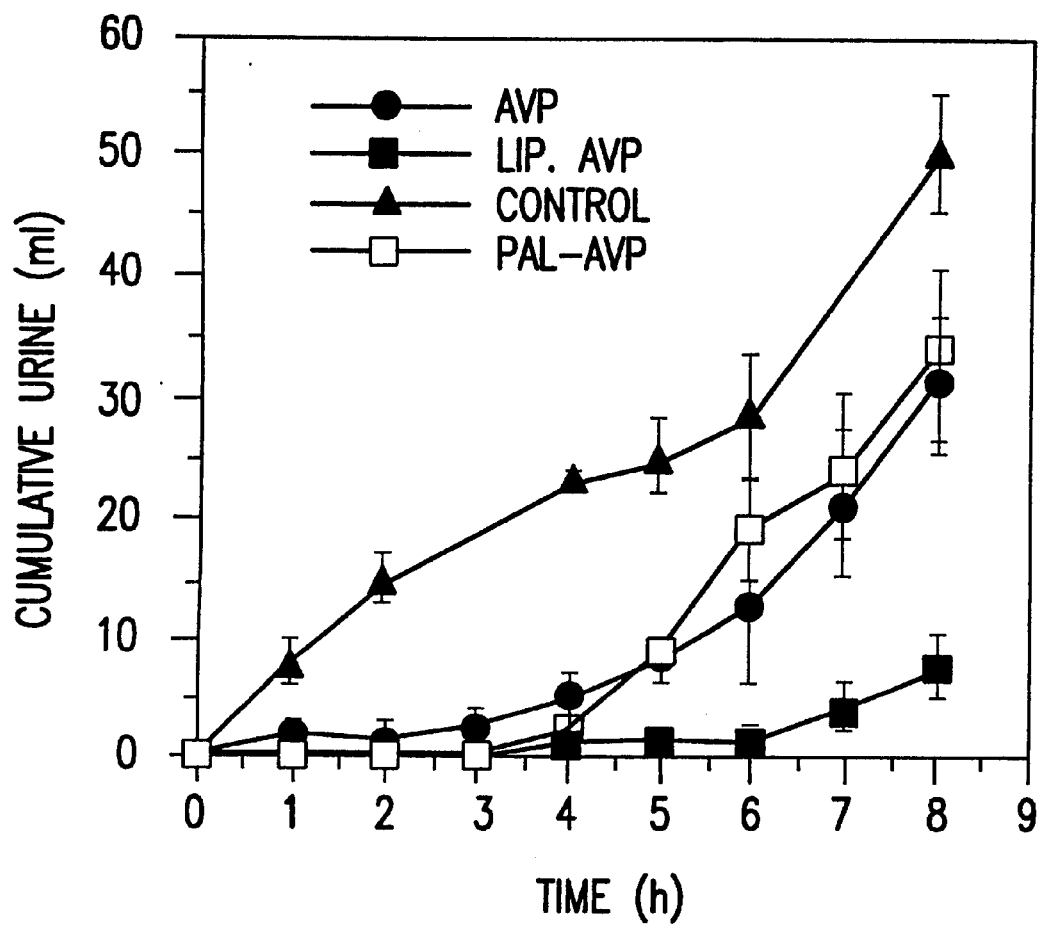
FIG. 2 shows the cumulative urine output of diabetic rats after subcutaneous injection of 5 µg/kg of AVP (arginine vasopressin), palmityl-AVP and REAL-AVP in accordance with the invention. The data show the mean and SD of measurements from 3 rats.
Figure 3:
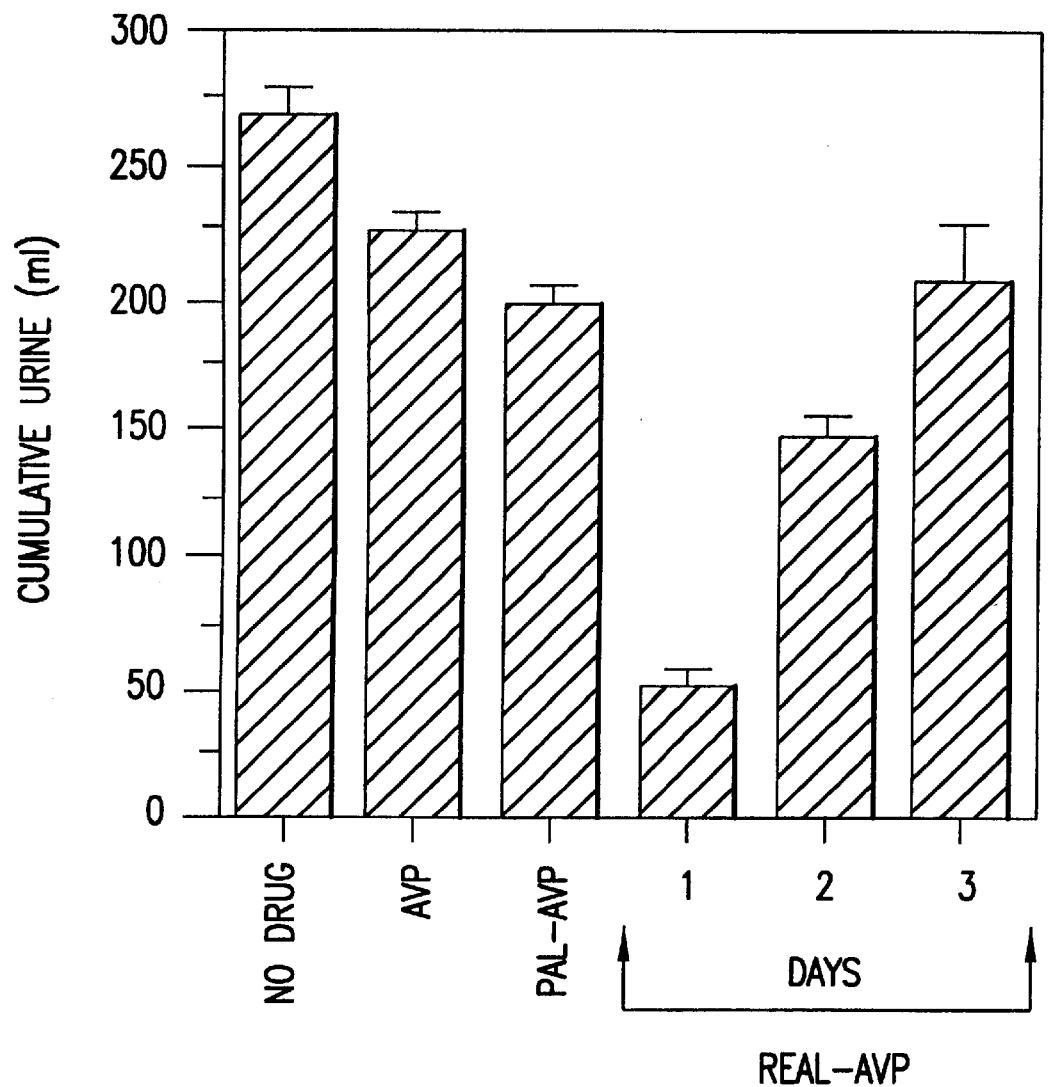
FIG. 3 shows the cumulative urine output of diabetic rats over 24 hours after subcutaneous injection of 5 µg/kg of AVP, palmityl-AVP and REAL-AVP in accordance with the invention. The data show the mean and SD of 3 experiments.

REAL-AVP was injected subcutaneously in animals (5 µg/kg) and urine was collected at different time points. FIG. 2 shows the cumulative volume of urine during the first 8 h after injection. AVP and Pal-AVP have similar effects with a delay in urine excretion of 4 h. A longer delay in urine excretion, up to 6 h, was observed after injection of REAL-AVP. Direct lipidization of AVP to palmitic acid, Pal-AVP, was not as effective as REAL-AVP. The amount of urine excretion was back to original 24 h after injection of Pal-AVP and AVP. However, the effect of REAL-AVP lasted for 3 days (FIG. 3).

It can be concluded that pH sensitive lipidization of AVP prolongs the biological activity of AVP.

Example 7

Preparation of Reversibly Lipidized Insulin (REAL-Insulin) Using Reagent A (Scheme 5)

Insulin (2 mg) was dissolved in 2 ml borate buffer (pH 10, 0.1M). Reagent A (1 mg, 2.1 μmol) was dissolved in 100 μl DMF and reacted with 1 ml (1 mg, about 0.14 μmol) insulin solution in an ice bath. The reaction mixture was stirred for 24 h at 4° C. and then dialyzed against 500 ml borate buffer (pH 10, 0.01M) for 24 h at 4° C. The volume of dialyzed REAL-insulin was adjusted to 2 ml using borate buffer (pH 10, 0.1M) to give a concentration of 0.5 mg/ml of REAL-Insulin. The volume of insulin stock solution (1 ml) was also adjusted to 2 ml to give a concentration of 0.5 mg/ml.

Example 8

The Effect of REAL-Insulin in Hyperglycemic Rats

Diabetes was induced in Sprague Dawley rats using i.v. injection of 60 mg/kg, streptozotocin. Solutions of 0.5 Unit/ml insulin or REAL-insulin in borate buffer (pH 10, 0.1M) were prepared. Rats were fasted 16 h prior to the experiment and were injected subcutaneously 0.5 Unit/kg of insulin or REAL-insulin. The blood glucose level of rats was monitored at different time points for 9 h. After this time rats were fed and the blood glucose level was measured after 15 h of feeding. The rats were again fasted and blood glucose level was measured after 16 h. The period of fasting and feeding was continued for 3 days.

Figure 4:
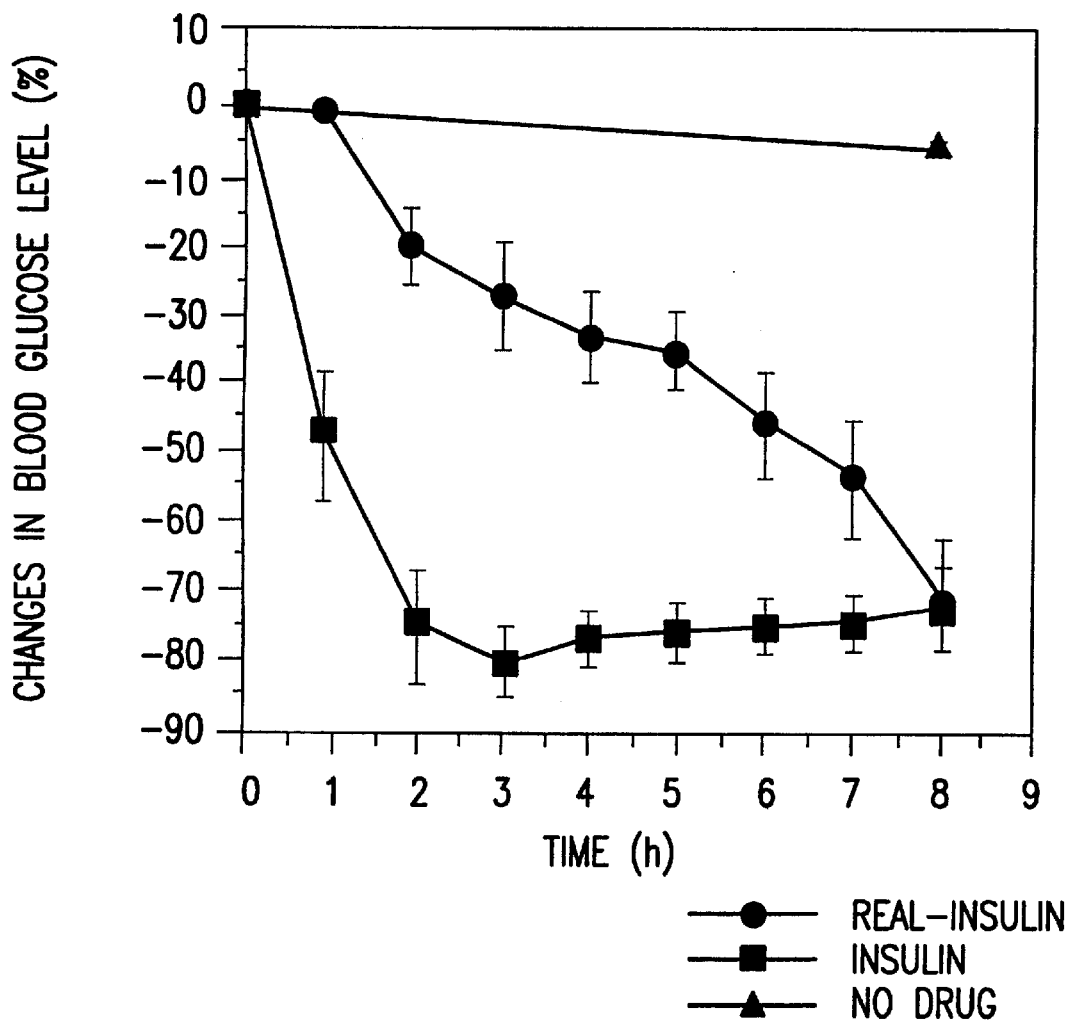
FIG. 4 shows the change in blood glucose level in fasted diabetic rats after subcutaneous injection of 0.35 U/kg of insulin compared with subcutaneous injection of 0.35 U/kg of REAL-insulin of the invention. The data show the mean and SD of measurements with 2 rats.
Figure 5:
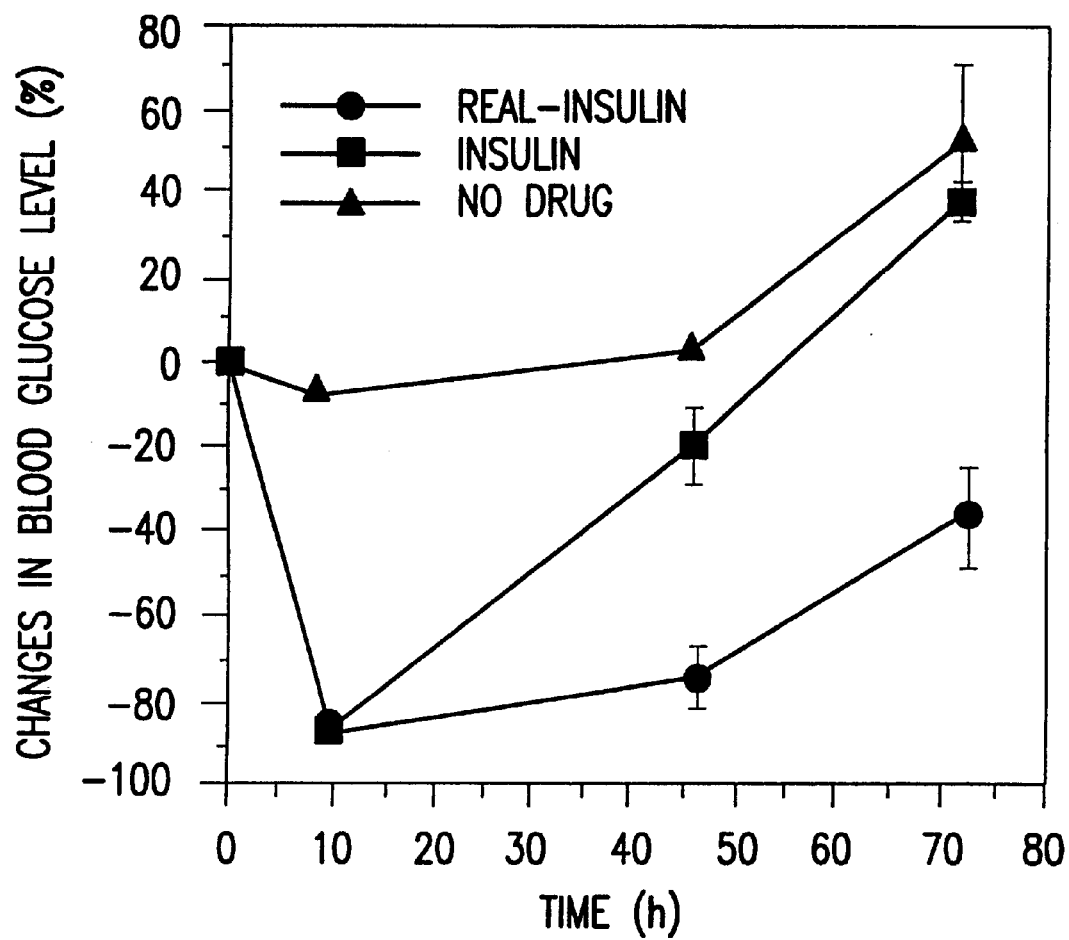
FIG. 5 shows the prolonged effect on blood glucose levels in fasted diabetic rats of subcutaneous injection of 0.5 U/kg insulin compared with subcutaneous injection of 0.5 U/kg REAL-insulin of the invention. The data show the mean and SD of measurements with 2 rats.
Figure 6:
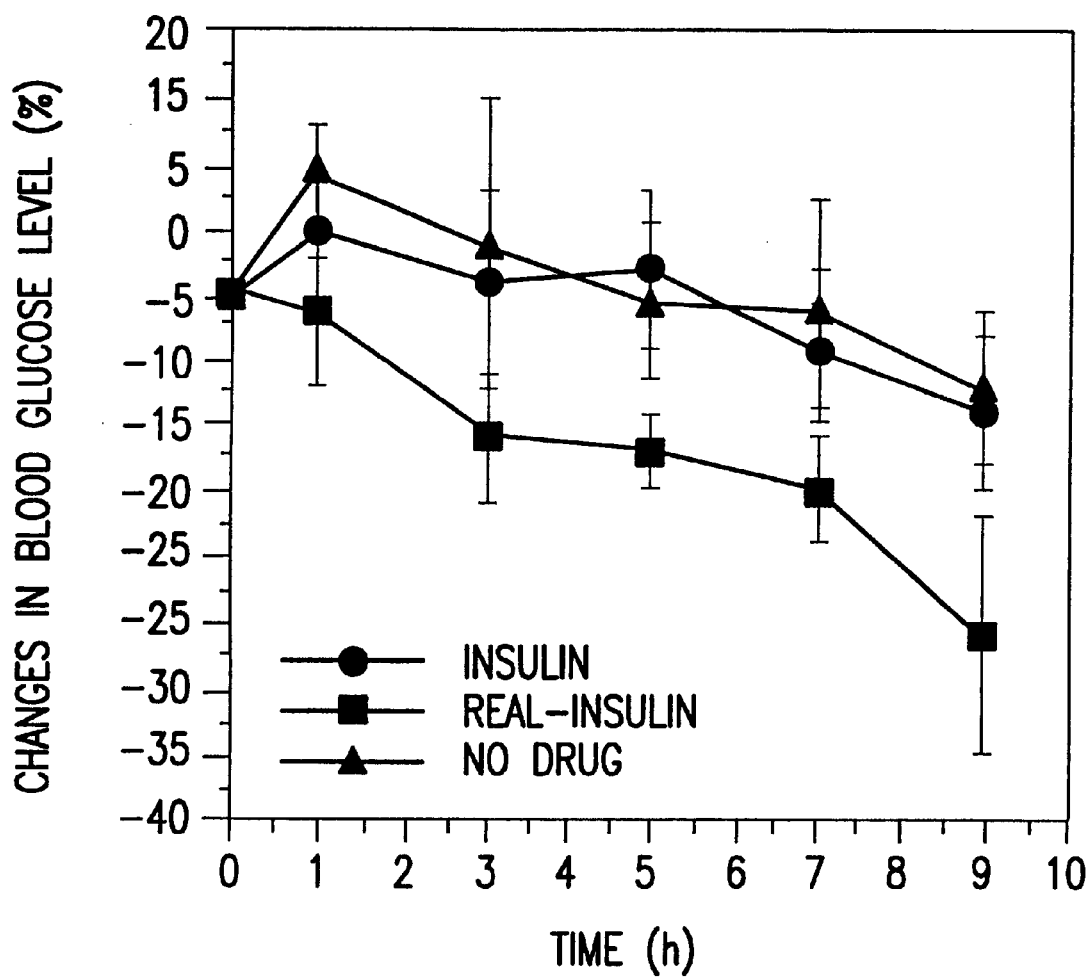
FIG. 6 shows the short-term effect on blood glucose level of fasted diabetic rats after oral administration of 10 U/kg REAL-insulin, insulin and placebo. The data show the mean and SD of measurements with four rats.

The blood glucose level of rats was increased one week after inducing diabetes from an average of 100 mg/dl to 420 mg/dl (non-fasted rats). In insulin-treated rats, significant drop in blood glucose level was observed within the first hour. However, in REAL-insulin treated rats, there was no changes in blood glucose level within the first hour and a significant drop in blood glucose was observed first 2 h after the injection (FIG. 4). This is possibly due to the time required for REAL-insulin to be hydrolyzed and to release free insulin. After injection of insulin the fast blood glucose level of rats was back to original within 24 h. However, in the case of the rats treated with REAL-insulin, the drug effect on the fast blood glucose level lasted for 3 days (FIG. 5). Fasted diabetic rats were also administered by oral means 10 U/kg of insulin, REAL-insulin and placebo. Rats were fasted 16 h prior to oral administration. A water/oil microemulsion was used as the drug carrier. FIG. 6 shows no significant reduction in blood glucose level was observed after oral administration of insulin or placebo. However, in rats treated with REAL-insulin, a 28% reduction of the blood glucose level was observed in 9 hours.

It can be concluded that by using REAL-insulin, the biological activity of insulin can be prolonged. Using an appropriate formulation, REAL-insulin may be administered orally to reduce blood glucose levels.

Having now fully described this invention, it will be understood to those of ordinary skill in the art that the same can be performed with a wide and equivalent range of conditions, formulations, and other parameters without affecting the scope of the invention or any embodiment thereof. All patents and publications cited herein are fully incorporated by reference herein in their entirety.

---

---

What is claimed is:

1. A compound of Formula I

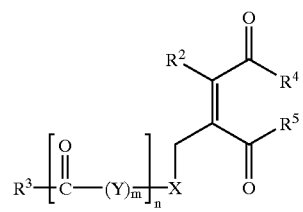

I in which $R^2$ is selected from the group consisting of hydrogen, lower alkyl, and aryl, wherein the lower alkyl and aryl are optionally substituted with one or more alkoxy, alkanoyl, nitro, cycloalkyl, alkenyl, alkynyl, acyloxy, lower alkyl or halogen;

$R^3$ is a naturally occurring lipid, a hydrophobic branched or unbranched hydrocarbon comprising about 4 to about 26 carbon atoms, a fatty acid or ester thereof, or a surfactant; one of $R^4$ and $R^5$ is a biologically active amino group-containing substance selected from the group consisting of an amine-containing drug, a natural or unnatural amino acid, a peptide and a protein and the other of $R^4$ and $R^5$ is $OR^6$ where $R^6$ is selected from the group consisting of hydrogen, an alkali metal and a negative charge;

X is oxygen or sulfur;

Y is a bridging natural or unnatural amino acid;

n is zero or 1; and m is an integer from zero to 10.

2. A compound according to claim 1, wherein $R^2$ is methyl and X is sulfur.

3. A compound according to claim 1, wherein n=0, m=0 and $R^3$ is a straight or branched-chain hydrocarbon having 4 to 26 carbon atoms.

4. A compound according to claim 3, wherein said straight or branched-chain hydrocarbon has 5 to 19 carbon atoms.

5. A compound according to claim 4, wherein said straight or branched-chain hydrocarbon together with the carbonyl group to which $R^3$ is bonded is selected from the group consisting of palmityl, oleyl, stearyl, lauryl and myristyl.

6. A compound according to claim 1, wherein Y is a natural amino acid.

7. A compound according to claim 1, wherein said amine-containing drug is tyramine.

8. A compound according to claim 1, wherein said peptide is selected from the group consisting of arginine vasopressin and insulin.

9. A compound according to claim 1, wherein n=0, m=0 and $R^3$ is cholic acid.

10. A compound according to claim 1, wherein n=0, m=0 and $R^3$ is deoxycholic acid.

11. A pharmaceutical composition comprising:
(a) the compound of claim 1; and
(b) a pharmaceutically acceptable carrier.

12. A tablet or dragee core comprising:
(a) the compound of claim 1; and
(b) a pharmaceutically acceptable carrier;
wherein the tablet or dragee core is coated with an enteric coating.

13. A compound of Formula II

II in which $R^2$ is selected from the group consisting of hydrogen, lower alkyl, and aryl, wherein the lower alkyl and aryl are optionally substituted with one or more alkoxy, alkanoyl, nitro, cycloalkyl, alkenyl, alkynyl, acyloxy, lower alkyl or halogen;

$R^3$ is a naturally occurring lipid, a hydrophobic branched or unbranched hydrocarbon comprising about 4 to about 26 carbon atoms, a fatty acid or ester thereof, or a surfactant;

X is oxygen or sulfur;

Y is a bridging natural or unnatural amino acid;

n is zero or 1; and m is an integer from zero to 10.

14. A compound according to claim 13, wherein $R^2$ is methyl and X is sulfur.

15. A compound according to claim 13, wherein n=0, m=0 and $R^3$ is a straight or branched-chain hydrocarbon of 4 to 26 carbon atoms.

16. A compound according to claim 15, wherein said straight or branched-chain hydrocarbon is of 5 to 19 carbon atoms.

17. A compound according to claim 15, wherein said straight or branched-chain hydrocarbon together with the neighboring carbonyl group is selected from the group consisting of palmityl, oleyl, stearyl, cholate and deoxycholate.

18. A compound according to claim 13, wherein Y is a natural amino acid.

19. A compound of Formula III

III or a pharmaceutically acceptable salt thereof;

in which $R^2$ is selected from the group consisting of hydrogen, lower alkyl, and aryl, wherein the lower alkyl and aryl are optionally substituted with one or more alkoxy, alkanoyl, nitro, cycloalkyl, alkenyl, alkynyl, acyloxy, lower alkyl or halogen;

$R^3$ is a naturally occurring lipid, a hydrophobic branched or unbranched hydrocarbon comprising about 4 to about 26 carbon atoms, a fatty acid or ester thereof, or a surfactant;

X is oxygen or sulfur;

Y is a bridging natural or unnatural amino acid;

n is zero or 1; and m is an integer from zero to 10.

20. A compound according to claim 19, wherein $R^2$ is methyl and X is sulfur.

21. A compound according to claim 19, wherein n=0, m=0 and $R^3$ is a straight or branched-chain hydrocarbon of 4 to 26 carbon atoms.

22. A compound according to claim 21, wherein said straight or branched-chain hydrocarbon is of 5 to 19 carbon atoms.

23. A compound according to claim 22, wherein said straight or branched-chain hydrocarbon together with the neighboring carbonyl group is selected from the group consisting of lauryl, myristyl, palmityl, oleyl, stearyl, cholate and deoxycholate.

24. A compound according to claim 19, wherein Y is a natural amino acid.

* * * * *